United States Patent
McChesney et al.

(10) Patent No.: US 8,440,714 B2
(45) Date of Patent: May 14, 2013

(54) ACID-LABILE LIPOPHILIC PRODRUGS OF CANCER CHEMOTHERAPEUTIC AGENTS

(75) Inventors: James D. McChesney, Etta, MS (US); John T. Henri, Longmont, CO (US); Sylesh Kumar Venkataraman, Broomfield, CO (US); Mahesh Kumar Gundluru, Cordova, TN (US)

(73) Assignee: Arbor Therapeutics, LLC, Etta, MI (US)

( * ) Notice: Subject to any disclaimer, the term of this patent is extended or adjusted under 35 U.S.C. 154(b) by 0 days.

(21) Appl. No.: 13/489,247

(22) Filed: Jun. 5, 2012

(65) Prior Publication Data

US 2012/0309819 A1    Dec. 6, 2012

Related U.S. Application Data

(60) Provisional application No. 61/493,827, filed on Jun. 6, 2011, provisional application No. 61/496,367, filed on Jun. 13, 2011.

(51) Int. Cl.
*A01N 43/16* (2006.01)
*A01N 43/08* (2006.01)
*A01N 43/02* (2006.01)

(52) U.S. Cl.
USPC ............ 514/449; 514/453; 514/461; 514/473

(58) Field of Classification Search .................. 514/449, 514/453, 461, 473
See application file for complete search history.

(56) References Cited

U.S. PATENT DOCUMENTS

| | | | |
|---|---|---|---|
| 6,191,290 B1 | 2/2001 | Safavy | |
| 6,825,166 B2 * | 11/2004 | McChesney et al. | 514/1.2 |
| 7,153,946 B2 * | 12/2006 | McChesney et al. | 536/6.4 |
| 2008/0207743 A1 | 8/2008 | Lamb et al. | |
| 2011/0135712 A1 | 6/2011 | McChesney et al. | |
| 2011/0318334 A1 | 12/2011 | McChesney et al. | |

OTHER PUBLICATIONS

Safavy et al., "Single-Drug Multiligand Conjugates: Synthesis and Preliminary Cytotoxicity Evaluation of a Paclitaxel-Dipeptide "Scorpion" Molecule", May/Jun. 2006, Bioconjugate Chemistry, vol. 17(3); pp. 565-570.*

* cited by examiner

*Primary Examiner* — My-Chau T Tran
(74) *Attorney, Agent, or Firm* — Hamilton DeSanctis & Cha, LLP; Sam L. Nguyen

(57) ABSTRACT

The present application discloses an acid labile lipophilic molecular conjugate of cancer chemotherapeutic agents and methods for reducing or substantially eliminating the side effects of chemotherapy associated with the administration of a cancer chemotherapeutic agent to a patient in need thereof.

15 Claims, 6 Drawing Sheets

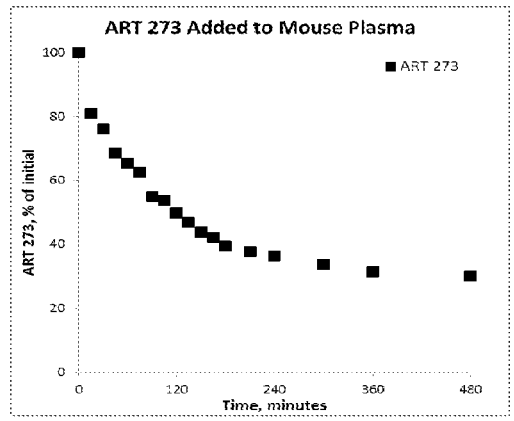
Figure 1: ART 273 Added to Mouse Plasma
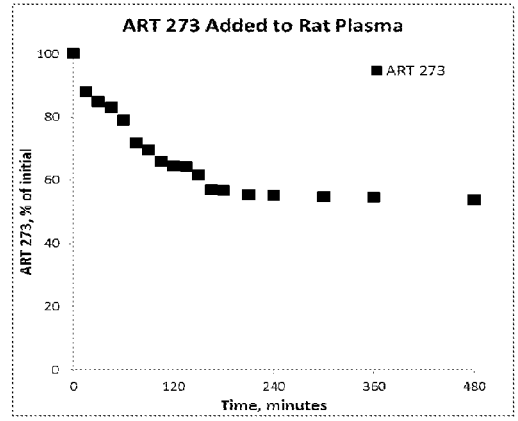
Figure 2: ART 273 Added to Rat Plasma
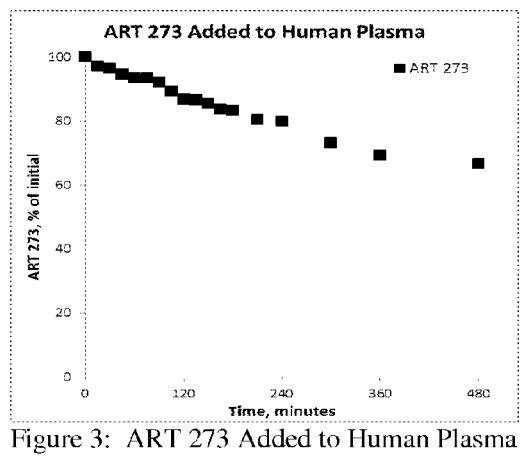
Figure 3: ART 273 Added to Human Plasma
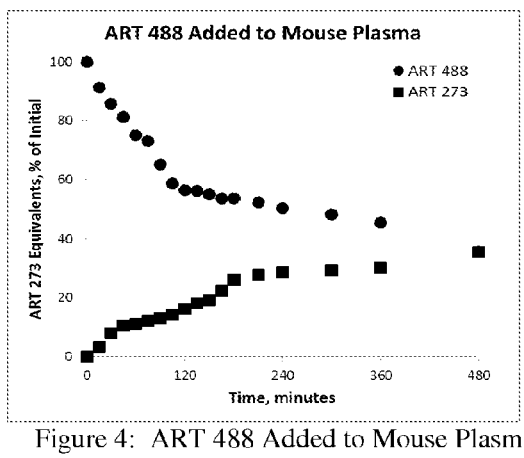
Figure 4: ART 488 Added to Mouse Plasma
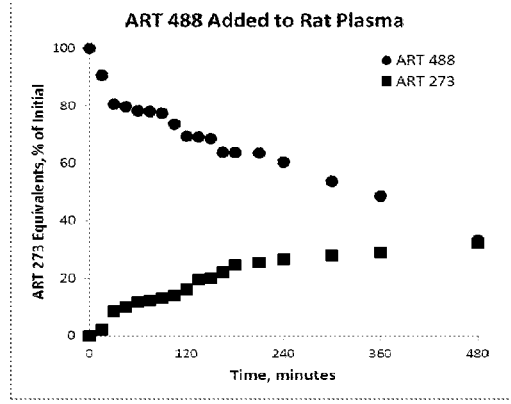
Figure 5: ART 488 Added to Rat Plasma
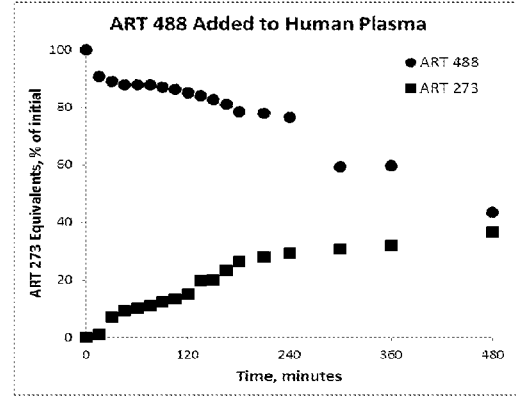
Figure 6: ART 488 Added to Human Plasma

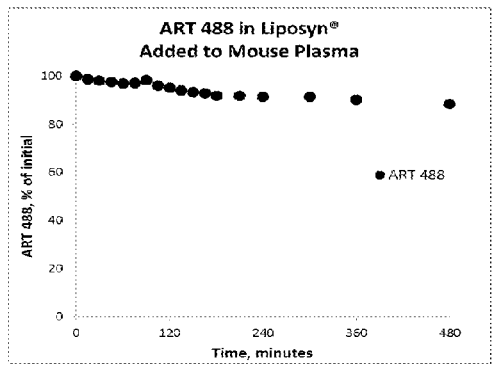
Figure 7: ART 488 in Liposyn® added to Mouse Plasma;
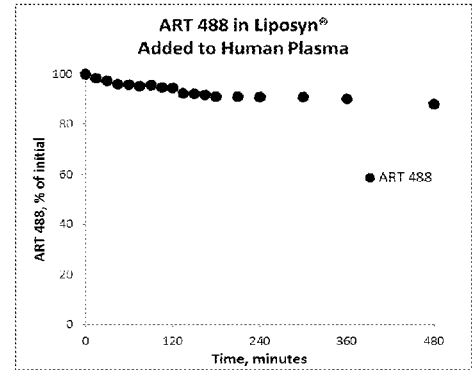
Figure 8: ART 488 in Liposyn® added to Human Plasma
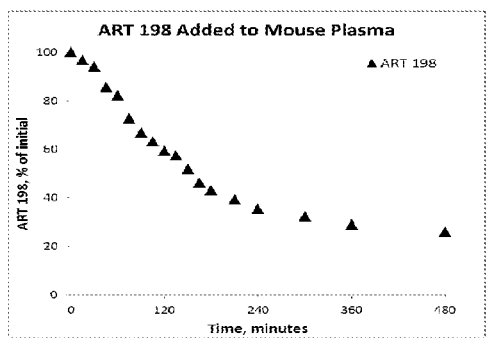
Figure 9: ART 198 Added to Mouse Plasma
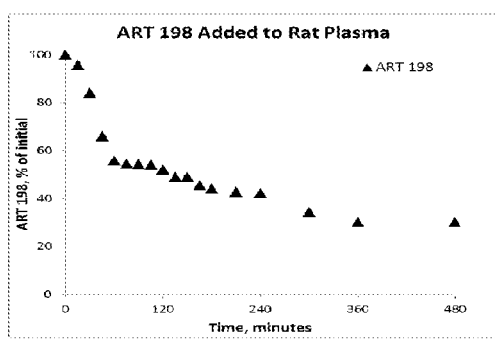
Figure 10: ART 198 Added to Rat Plasma
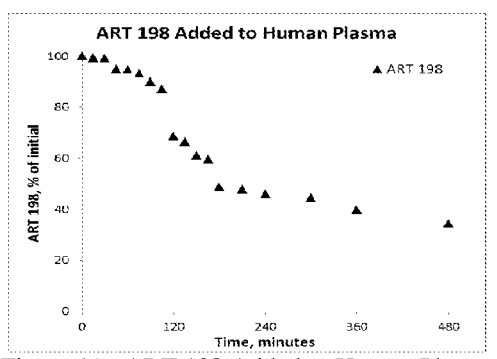
Figure 11: ART 198 Added to Human Plasma
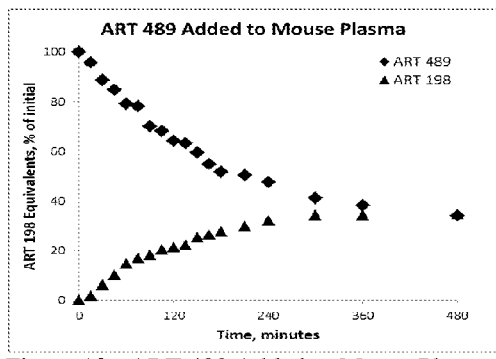
Figure 12: ART 489 Added to Mouse Plasma

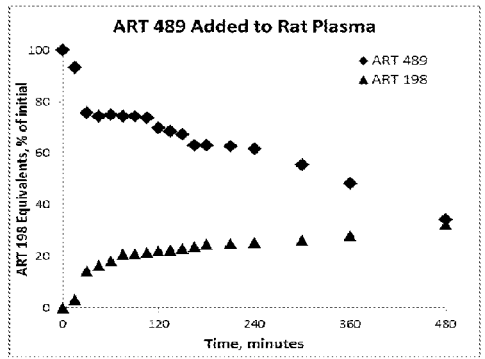
Figure 13: ART 489 Added to Rat Plasma
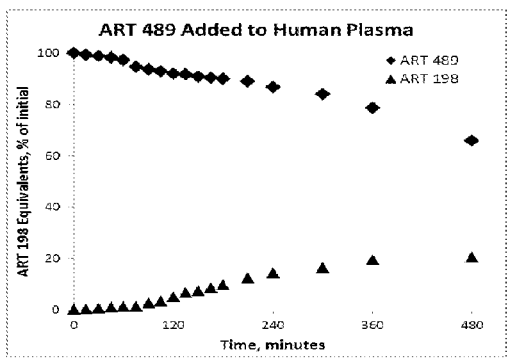
Figure 14: ART 489 Added to Human Plasma
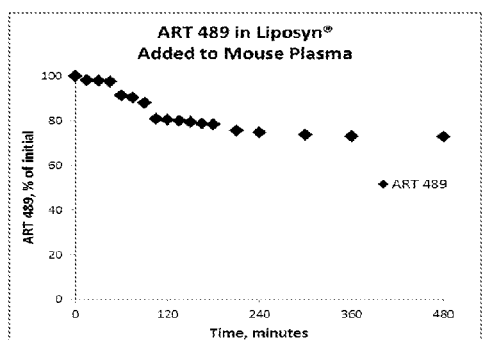
Figure 15: ART 489 in Liposyn® added to Mouse Plasma;
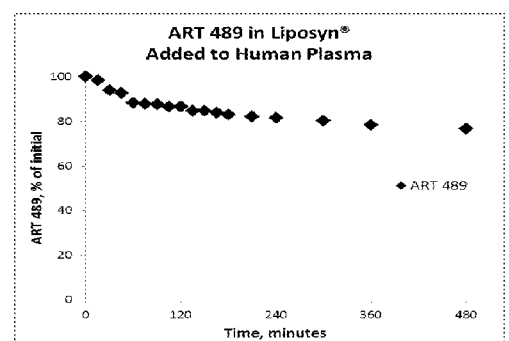
Figure 16: ART 489 in Liposyn® Added to Human Plasma
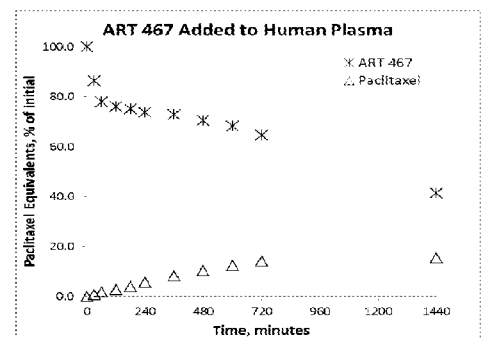
Figure 17: ART 467 Added to Human Plasma Acid Labile Lipophilic Molecular Conjugates
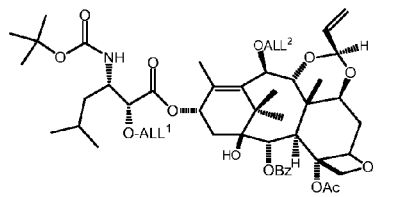
ALLMC of a 10-beta-taxane analog (19a)
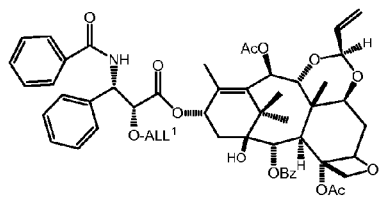
ALLMC of a 10-beta taxane analog (19b)
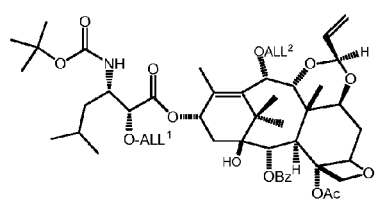
ALLMC of a 10-alpha taxane analog (19c)
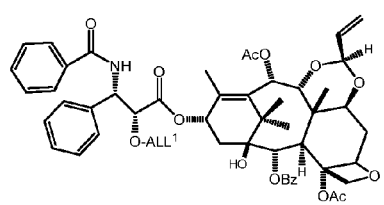
ALLMC of a 10-alpha analog (19d)
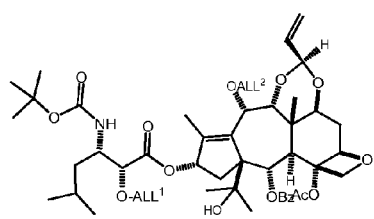
ALLMC of a 10-alpha abeo-taxane analog (19e)
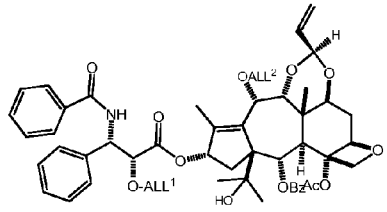
ALLMC of a 10-alpha abeo-taxane analog (19f)
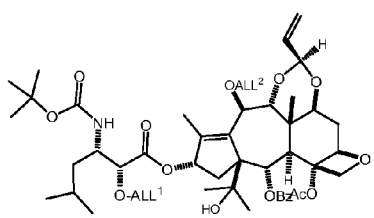
ALLMC of a 10-beta abeo-taxane analog (19g)
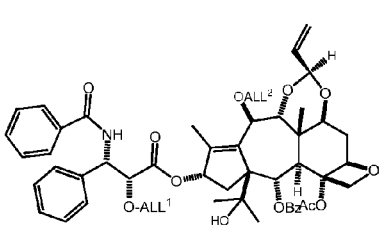
ALLMC of a 10-beta abeo-taxane analog (19h)
FIGURE 19

Acid Labile Lipophilic Molecular Conjugates

ACID-LABILE LIPOPHILIC PRODRUGS OF CANCER CHEMOTHERAPEUTIC AGENTS

CROSS REFERENCE TO RELATED APPLICATIONS

This application claims the benefit of U.S. Provisional Application No. 61/493,827 filed Jun. 6, 2011 and U.S. Provisional Application No. 61/496,367 filed Jun. 13, 2011, the full contents of which are incorporated herein by reference.

FIELD OF THE INVENTION

The present invention generally relates to chemical compounds and methods for use in treating patients. More particularly, the present invention is directed to molecular conjugates for use in cancer treatment. Specifically, the present invention relates to acid-labile, lipophilic conjugates, methods and intermediates useful in the formation thereof, and methods for treating a patient therewith.

BACKGROUND OF THE INVENTION

A number of anti-cancer drug are currently in the market for the treatment of various cancers. For example, paclitaxel and docetaxel are two promising anti-cancer drugs used to treat breast and ovarian cancers, and which hold promise for the treatment of various other cancers such as skin, lung, head and neck carcinomas. Other promising chemotherapeutic agents are being developed or tested for treatment of these and other cancers. Compounds such as paclitaxel, docetaxel and other taxanes, camptothecins, epothilones and quassinoids, as well as other compounds exhibiting efficacy in cancer treatment, are of considerable interest. Of special interest are natural product drugs and their synthetic analogs with demonstrated anticancer activity in vitro and in vivo.

However, many identified anti-cancer compounds present a number of difficulties with their use in chemotherapeutic regimens. A major problem with the use of such chemotherapeutic agents in cancer treatment is the difficulty targeting cancer tissues, without adversely affecting normal, healthy tissues. For example, paclitaxel exerts its antitumor activity by interrupting mitosis and the cell division process, which occurs more frequently in cancer cells, than in normal cells. Nonetheless, a patient undergoing chemotherapy treatment may experience various adverse effects associated with the interruption of mitosis in normal, healthy cells.

Targeted cancer therapies that can selectively kill cancer cells without harming other cells in the body would represent a major improvement in the clinical treatment of cancer. Reports of targeting drugs using antibodies have appeared in the literature since 1958. Targeting drugs by conjugation to antibodies for selective delivery to cancer cells has had limited success due to the large size of antibodies (MW=125-150 kilodaltons) and thus their relative inability to penetrate solid tumors.

An alternative strategy comprises the use of smaller targeting ligands and peptides, which recognize specific receptors unique to or overexpressed on tumor cells, as the targeting vector. Such constructs have molecular weights of 2-6 kilodaltons, which allow ready penetration throughout solid tumors.

Accordingly, it would be highly desirable to develop novel compounds and methods for use in directly targeting cancer cells with chemotherapeutic agents in cancer treatment regimens. This, in turn, could lead to reduction or elimination of toxic side effects, more efficient delivery of the drug to the targeted site, and reduction in dosage of the administered drug and a resulting decrease in toxicity to healthy cells and in the cost of the chemotherapeutic regimen.

One particular approach of interest is the use of anticancer drug moieties that have been conjugated to tumor molecules. For example, U.S. Pat. No. 6,191,290 to Safavy discusses the formation and use of a taxane moiety conjugated to a receptor ligand peptide capable of binding to tumor cell surface receptors. Safavy in particular indicates that such receptor ligand peptides might be a bombesin/gastrin-releasing peptide (BBN/GRP) receptor-recognizing peptide (BBN [7-13]), a somatostatin receptor-recognizing peptide, an epidermal growth factor receptor-recognizing peptide, a monoclonal antibody or a receptor-recognizing carbohydrate.

One important aspect of synthesizing these drug molecular conjugates is connecting these two units with a linker or linkers that provide conjugates with desired characteristics and biological activity, in particular, a conjugate that is stable in systemic circulation but releases cytotoxic agent once internalized into cancer cells or concentrated in the locally acidic tumor environment. Such an agent would be expected to exhibit lower toxicity to normal tissues. The resulting conjugate should also be sufficiently stable until it reaches the target tissue, and thus maximizing the targeting effect with reduced toxicity to normal, healthy tissue.

The blood-brain barrier (BBB) is a specialized physical and enzymatic barrier that segregates the brain from systemic circulation. The physical portion of the BBB is composed of endothelial cells arranged in a complex system of tight junctions which inhibit any significant paracellular transport. The BBB functions as a diffusion restraint selectively discriminating against substance transcytosis based on lipid solubility, molecular size and charge thus posing a problem for drug delivery to the brain. Drug delivery across the BBB is further problematic due to the presence of a high concentration of drug efflux transporters (e.g., P-glycoprotein, multi-drug resistant protein, breast cancer resistant protein). These transporters actively remove drug molecules from the endothelial cytoplasm before they even cross into the brain.

The methods that are currently employed for drug delivery in treatment of brain malignancies are generally nonspecific and inefficient. An additional problem to consider when treating brain diseases is the diffusion of the drug in its vehicle across the tumor or affected tissue. Mostly the size, as well as other physiologic characteristics of the vehicles that are currently in use for such delivery of drugs to the brain, hamper efficient diffusion of the drug through the diseased tissue. The lack of efficient drug diffusion affects the efficacy of the treatment.

Peptides have been extensively studied as carrier molecules for drug delivery to the brain in hope they could be employed as drug delivery vehicles. Peptides are, however, problematic due to their limited bioavailability. Even though methods to increase the bioavailability of such molecules have been intensively explored, they resulted in modest success at best.

Increased cell proliferation and growth is a trademark of cancer. The increase in cellular proliferation is associated with high turnover of cell cholesterol. Cells requiring cholesterol for membrane synthesis and growth may acquire cholesterol by receptor mediated endocytosis of plasma low density lipoproteins (LDL), the major transporter of cholesterol in the blood, or by de novo synthesis.

LDL is taken up into cells by a receptor known as the LDL receptor (LDLR); the LDL along with the receptor is endocytosed and transported into the cells in endosomes. The endosomes become acidified and this releases the LDL receptor from the LDL; the LDL receptor recycles to the surface where it can participate in additional uptake of LDL particles. There is a body of evidence that suggests that tumors in a variety of tissues have a high requirement for LDL to the extent that plasma LDLs are depleted. The increased import of LDL into cancerous cells is thought to be due to elevated LDL receptors (LDLR) in these tumors. Some tumors known to express high numbers of LDLRs include some forms of leukemia, lung tumors, colorectal tumors and ovarian cancer.

Comparative studies of normal and malignant brain tissues have shown a high propensity of LDLRs to be associated with malignant and/or rapidly growing brain cells and tissues. Some studies suggest that rapidly growing brain cells such as those seen in early development and in aggressively growing brain tumors exhibit increased expression of LDLRs due to their increased requirement for cholesterol.

Among the problematic and inefficiently treated brain cancers is glioblastoma multiforme (GBM). This devastating brain tumor is 100% fatal. Moreover, over 85% of total primary brain cancer-related deaths are due to GBM. Current therapies rely on a multimodal approach including neurosurgery, radiation therapy and chemotherapy. Even the best efforts using these approaches have resulted in only a modest increase in survival time for patients afflicted with this tumor.

GBM being gliomas of the highest malignancy is characterized by uncontrolled, aggressive cell proliferation and general resistance to conventional therapies. GBM cells in culture have high numbers of low density lipoprotein receptors (LDLR). Since this receptor is nearly absent in neuronal cells and normal glial cells, it represents an ideal target for the delivery of therapeutic agents such as cytotoxins or radiopharmaceuticals. Efforts to improve existing therapies or to develop new ones have not been successful and the outcome of treatment for malignant gliomas is only modest, at best, with a median survival time of approximately 10 months.

Unlike normal brain cells that have few LDL receptors, GBM cells in culture have high numbers of LDL receptors on their surface. Other cancers are likely to also have high expression of LDLR due to the highly proliferative nature of the cancerous tissue and need for cholesterol turnover. This suggests that the LDL receptor is a potential unique molecular target in GBM and other malignancies for the delivery of anti-tumor drugs via LDL particles.

Maranhão and coworkers have demonstrated that a cholesterol-rich microemulsion or nanoparticle preparation termed LDE concentrates in cancer tissues after injection into the bloodstream. D. G. Rodrigues, D. A. Maria, D. C. Fernandes, C. J. Valduga, R. D. Couto, O. C. Ibanez and R. C. Maranhão Improvement of paclitaxel therapeutic index by derivatization and association to a cholesterol-rich microemulsion: in vitro and in vivo studies. *Cancer Chemotherapy and Pharmacology* 55: 565-576 (2005). The cytotoxicity, pharmacokinetics, toxicity to animals and therapeutic action of a paclitaxel lipophilic derivative associated to LDE were compared with those of commercial paclitaxel. Results showed that LDE-paclitaxel oleate was stable. The cytostatic activity of the drug in the complex was diminished compared with the commercial paclitaxel due to the cytotoxicity of the vehicle Cremophor EL used in the commercial formulation. Maranhão and coworkers showed LDE-paclitaxel oleate is a stable complex and compared with paclitaxel, toxicity is considerably reduced and activity is enhanced which may lead to improved therapeutic index in clinical use.

Capturing the great potential of selective and specific delivery of chemotherapeutic compounds to cancer tissues via their over expression of LDL receptors and consequent high uptake of LDL particles from the systemic circulation, requires that the cancer chemotherapeutic agent have high lipophilicity so as to remain entrapped in the lipid core of the LDL particle and not diffuse into the plasma to lead to toxic side effects from exposure of normal tissues to the agent. Further, once the LDL particle with its chemotherapeutic payload has entered the cancer cell via LDL receptor mediated uptake into the acidic environment of the endosome, the LDL receptor is disassociated from the LDL particle and is recycled to the cell surface and the LDL particle releases its lipid contents and its lipophilic chemotherapeutic agent to the enzymes and acidic environment of the endosome. Few cancer chemotherapeutic agents are intrinsically sufficiently lipophilic to be retained adequately within the lipid core of the LDL particle. This creates a need for suitable lipophilic derivatives of the cancer chemotherapeutic agent which have high stability in normal systemic circulation and retention in the lipid core of the LDL particles but readily release the active chemotherapeutic agent in the acidic environment of the endosome. The compounds of the present invention address this need.

DEFINITIONS

As used herein, the term "alkyl", alone or in combination, refers to an optionally substituted straight-chain or branched-chain alkyl radical having from 1 to 22 carbon atoms (e.g. $C_1$-$C_{22}$ alkyl or $C_{1-22}$ alkyl). Examples of alkyl radicals include methyl, ethyl, n-propyl, isopropyl, n-butyl, isobutyl, sec-butyl, tert-butyl, tert-amyl, pentyl, hexyl, heptyl, octyl and the like. In certain embodiments, the alkyl group, such as a $C_1$-$C_{22}$ alkyl or $C_5$-$C_{22}$ alkyl, may also include one or more double bonds in the alkyl group, and may also referred to as in a $C_1$-$C_{22}$ alkenyl or $C_5$-$C_{22}$ alkenyl group.

The term "alkenyl", alone or in combination, refers to an optionally substituted straight-chain or branched-chain hydrocarbon radical having one or more carbon-carbon double-bonds and having from 2 to about 22 carbon atoms. Examples of alkenyl radicals include ethenyl, propenyl, 1,4-butadienyl and the like.

The term "alkoxy" refers to an alkyl ether radical wherein the term alkyl is defined as above. Examples of alkoxy radicals include methoxy, ethoxy, n-propoxy, isopropoxy, n-butoxy, iso-butoxy, sec-butoxy, tert-butoxy and the like.

The term "diastereoisomer" refers to any group of four or more isomers occurring in compounds containing two or more asymmetric carbon atoms. Compounds that are stereoisomers of one another, but are not enantiomers are called diastereoisomers.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. Protecting group chemistry has been reviewed (Greene, T. W.; Wuts, P. G. M. Protective Groups in Organic Synthesis, 4th ed.; Wiley: New York, 2007). Exemplary silyl groups for protection of hydroxyl groups include TBDMS (tert-butyldimethylsilyl), NDMS (2-norbornyldimethylsilyl), TMS (trimethylsilyl) and TES (triethylsilyl). Exemplary NH-protecting groups include benzyloxycarbonyl, t-butoxycarbonyl and triphenylmethyl.

The terms "taxanes," "taxane derivatives," and "taxane analogs" etc . . . are used interchangeably to mean compounds relating to a class of antitumor agents derived directly or semi-synthetically from Taxus brevifolia, the Pacific yew.

Examples of such taxanes include paclitaxel and docetaxel and their natural as well as their synthetic or semi-synthetic derivatives.

"Pharmaceutically acceptable excipient" or "pharmaceutically acceptable salts" as used herein, means the excipient or salts of the compounds disclosed herein, that are pharmaceutically acceptable and provides the desired pharmacological activity. These excipients and salts include acid addition salts formed with inorganic acids such as hydrochloric acid, hydrobromic acid, phosphoric acid, and the like. The salt may also be formed with organic acids such as acetic acid, propionic acid, hexanoic acid, glycolic acid, lactic acid, succinic acid, malic acid, citric acid, benzoic acid and the like.

"Therapeutically effective amount" means a drug amount that elicits any of the biological effects listed in the specification.

SUMMARY OF THE INVENTION

In one embodiment, there is provided new and useful compositions of molecular conjugates of hydroxyl-bearing cancer chemotherapeutic agents (HBCCA). In another embodiment, there is provided compositions of acid labile, lipophilic molecular conjugates of cancer chemotherapeutic agents for use in treating cancer. In another embodiment, there is provided intermediate compounds for use in forming molecular conjugates, such as acid labile, lipophilic pro-drug conjugates, for use in treating cancer. In another embodiment, there is provided efficient methods for the preparation of acid labile, lipophilic drug conjugates. In another embodiment, there is provided methods for administering chemotherapeutic agents to patients that reduce or substantially eliminate side effects conventionally experienced by cancer patients. In another embodiment, there is provided methods for concentrating chemotherapeutic agents in cancer cells of a patient.

In one embodiment, there is provided an acid labile lipophilic molecular conjugate (ALLMC) of the formula 1, 1.1 or formula 2:

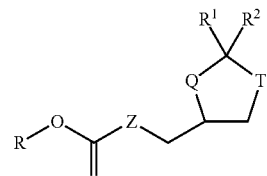

1

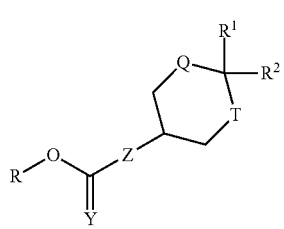

1.1

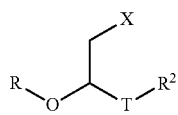

2 wherein: R is a hydroxyl bearing cancer chemotherapeutic agent; for formula 1 or 1.1 $R^1$ is hydrogen, $C_1$-$C_4$ alkyl or $C_5$-$C_{22}$ alkyl; $R^2$ is $C_5$-$C_{22}$ alkyl; Y is selected from O, NR' or S wherein R' is hydrogen or $C_1$-$C_6$ alkyl; Z is O or S; Q is O or S; and T is O or S; for formula 2: $R^2$ is a $C_1$-$C_{22}$ alkyl; T is O or S; and X is hydrogen or a leaving group selected from the group consisting of mesylates, sulfonates and halogen (Cl, Br and I); and their isolated enantiomers, diastereoisomers or mixtures thereof, or a pharmaceutically acceptable salt thereof. The compound 1.1 includes the pure syn isomer, the pure anti isomer and mixtures of syn- and anti-isomers, and their diastereomers.

In another embodiment, there is provided the above acid labile lipophilic molecular conjugate of the formula 1 or 1.1 wherein: R is a hydroxyl bearing cancer chemotherapeutic agent; $R^1$ is hydrogen, $C_1$-$C_4$ alkyl or $C_5$-$C_{22}$ alkyl; $R^2$ is $C_5$-$C_{22}$ alkyl; Y is O or S; Z is O; Q is O; and T is O. In one aspect of the acid labile lipophilic molecular conjugate of the formula 2 wherein: $R^2$ is $C_5$-$C_{22}$ alkyl; T is O; and X is hydrogen or selected from the group consisting of Cl, Br and I. In another variation, $R^2$ is $C_9$-$C_{22}$. In another aspect of the above acid labile lipophilic molecular conjugate comprising the formula 1a, 1b or formula 2a:

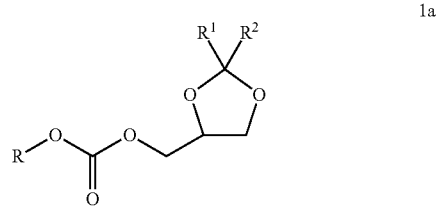

1a

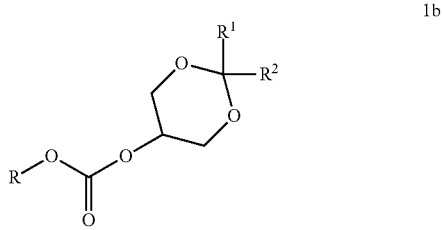

1b

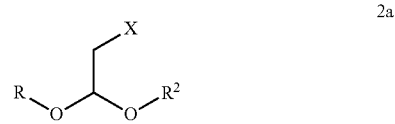

2a wherein: R is a hydroxyl bearing cancer chemotherapeutic agent (HBCCA);

for formula 1a or 1b $R^1$ is hydrogen, $C_1$-$C_4$ alkyl or $C_5$-$C_{22}$ alkyl; and $R^2$ is $C_5$-$C_{22}$ alkyl;

and for formula 2a: $R^2$ is $C_1$-$C_{22}$ alkyl; and X is hydrogen or is selected from the group consisting of Cl, Br and I. In one variation of the compound that is the carbonate (i.e., —OC(O)O—) of the formula 1a or 1b the compound is the corresponding sulfonate (i.e., —OS(O)O—) of the formula 1a wherein the carbonate group is replaced by a sulfonate group. The compound 1b includes the pure syn isomer, the pure anti isomer and mixtures of syn and anti isomers, and their diastereomers.

In another variation of the compound of the formula 1, 2, 1a and 2a, $R^1$ is hydrogen or $C_1$-$C_4$ alkyl or $C_5$-$C_{22}$ alkyl, and $R^2$ is the carbon residue of an unsaturated fatty acid, such as the carbon residue selected from the group consisting of the $C_{19}$ residue of eicosenoic acid (including the cis isomer, trans isomer and mixtures of isomers), $C_{17}$ residue of oleic acid and the $C_{17}$ residue of elaidic acid. As used herein, the "carbon residue" (e.g., $C_{17}$ residue, $C_{19}$ residue etc . . . ) of the fatty acid means the carbon chain of the fatty acids excluding the carboxyl carbon.

In another aspect of the above acid labile lipophilic molecular conjugate, the hydroxyl bearing cancer chemotherapeutic agent is selected from the group consisting of taxanes, abeo-taxanes, camptothecins, epothilones, cucurbitacins, quassinoids, anthracyclines, and their analogs and derivatives. In another aspect of the above acid labile lipophilic molecular conjugate, the hydroxyl bearing cancer chemotherapeutic agent is selected from the group consisting of aclarubicin, camptothecin, masoprocol, paclitaxel, pentostatin, amrubicin, cladribine, cytarabine, docetaxel, gemcitabine, elliptinium acetate, epirubicin, etoposide, formestane, fulvestrant, idarubicin, pirarubicin, topotecan, valrubicin and vinblastine. In another aspect of the above acid labile lipophilic molecular conjugate, the conjugate is selected from the compounds in FIGS. 18, 19 and 20. In one variation, only one of the groups -ALL$^1$, -ALL$^2$, -ALL$^3$ . . . to -ALL$^n$ is an -ALL group and the others are hydrogens. In another variation, two of the groups -ALL$^1$, -ALL$^2$, -ALL$^3$ . . . to -ALL$^n$ are -ALL groups.

In another embodiment, there is provided a pharmaceutical composition comprising: a) a therapeutically effective amount of a compound of the above, in the form of a single diastereoisomer; and b) a pharmaceutically acceptable excipient. In another aspect, the pharmaceutical composition is adapted for oral administration; or as a liquid formulation adapted for parenteral administration. In another aspect, the composition is adapted for administration by a route selected from the group consisting of orally, parenterally, intraperitoneally, intravenously, intraarterially, transdermally, intramuscularly, rectally, intranasally, liposomally, subcutaneously and intrathecally. In another embodiment, there is provided a method for the treatment of cancer in a patient comprising administering to the patient a therapeutically effective amount of a compound or composition of any of the above compound or composition, to a patient in need of such treatment. In one aspect of the method, the cancer is selected from the group consisting of leukemia, neuroblastoma, glioblastoma, cervical, colorectal, pancreatic, renal and melanoma. In another aspect of the method, the cancer is selected from the group consisting of lung, breast, prostate, ovarian and head and neck. In another aspect of the method, the method provides at least a 10%, 20%, 30%, 40%, or at least a 50% diminished degree of resistance expressed by the cancer cells when compared with the non-conjugated hydroxyl bearing cancer chemotherapeutic agent.

In another embodiment, there is provided a method for reducing or substantially eliminating the side effects of chemotherapy associated with the administration of a cancer chemotherapeutic agent to a patient, the method comprising administering to the patient a therapeutically effective amount of an acid labile lipophilic molecular conjugate of the formula 1, 1.1 or formula 2:

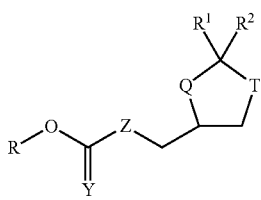

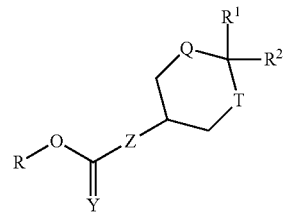

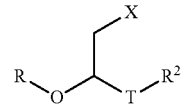

wherein: R is a hydroxyl bearing cancer chemotherapeutic agent; for formula 1 or 1.1: $R^1$ is hydrogen, $C_1$-$C_4$ alkyl or $C_5$-$C_{22}$ alkyl; $R^2$ is $C_5$-$C_{22}$ alkyl; Y is selected from O, NR' or S wherein R' is hydrogen or $C_1$-$C_6$ alkyl; Z is O or S; Q is O or S; and T is O or S; for formula 2: $R^2$ is $C_1$-$C_{22}$ alkyl; T is O or S; and X is hydrogen or a leaving group selected from the group consisting of mesylates, sulfonates and halogen (Cl, Br and I); and their isolated enantiomers, diastereoisomers or mixtures thereof. The compound 1.1 includes the pure syn isomer, the pure anti isomer and mixtures of syn and anti isomers, and their diastereomers. In one variation of the above, $R^2$ is $C_9$-$C_{22}$ alkyl. In one aspect, the method provides a higher concentration of the cancer chemotherapeutic agent in a cancer cell of the patient. In another aspect, the method delivers a higher concentration of the cancer chemotherapeutic agent in the cancer cell, when compared to the administration of a non-conjugated cancer chemotherapeutic agent to the patient, by at least 5%, 10%, 20%, 30%, 40% or at least 50%.

In another embodiment, there is provided a compound of the formula 3a or 3b:

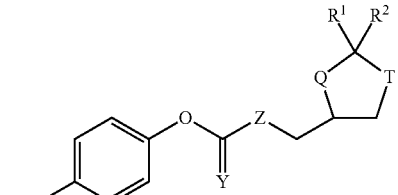

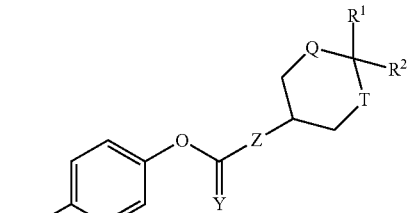

wherein: $R^1$ is hydrogen, $C_1$-$C_4$ alkyl or $C_5$-$C_{22}$ alkyl; $R^2$ is $C_5$-$C_{22}$ alkyl; Y is selected from O, NR' or S wherein R' is hydrogen or $C_1$-$C_6$ alkyl; Z is selected from O or S; Q is O or S; and T is O or S. In one aspect of the compound, $R^1$ is hydrogen or $C_1$-$C_4$ alkyl; $R^2$ is $C_5$-$C_{22}$ alkyl; Y is O or S; Z is O; Q is O; and T is O. The activated compound of the formula 3a or 3b may be used to prepare the acid labile lipophilic conjugate when the activated compound is condensed with a hydroxyl bearing cancer chemotherapeutic agent (HBCCA). As defined herein, the HBCCA is represented generically with the residue or group "R" in the formulae 1, 1a, 1b, 1.1, 2 and 2a, for example, and where the HBCCA is not coupled to form the acid labile, lipophilic molecular conjugates, then the HBCCA may also be generically represented as having the formula "R—OH" since the HBCCA may be functionalized by one or more hydroxyl (—OH) groups. Similarly, the acid labile lipophilic group (i.e., the "-ALL" group of the activated compound) that may be condensed with a HBCCA to form the acid labile, lipophilic molecular conjugate generically represented as "R—O-ALL." Accordingly, where more than one -ALL group is condensed or conjugated with a HBCCA group, then each -ALL group may be independently designated as -ALL$^1$, -ALL$^2$, -ALL$^3$ . . . to -ALL$^n$ where n is the number of available hydroxyl groups on the cancer chemotherapeutic agent that may be conjugated or couple with an -ALL group. As exemplified for the compound of formulae 1 and 2, for example, the HBCCA and the -ALL groups as designated, are shown below.

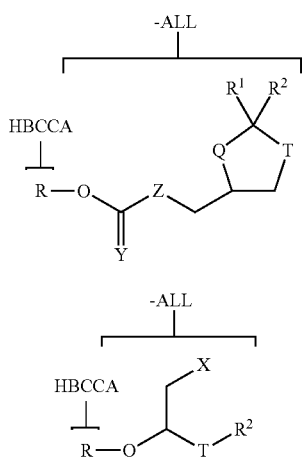

An example of an acid labile, lipophilic molecular conjugate (ALLMC), where the HBCCA group is paclitaxel having two -ALL groups, is depicted below:

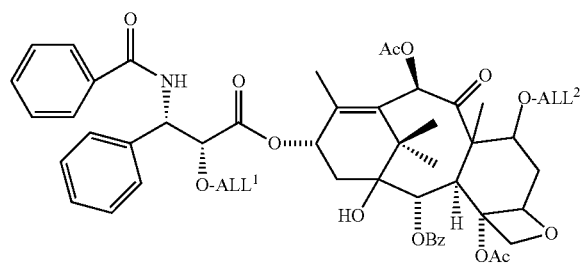

Acid Labile Lipophilic Molecular Conjugate of Paclitaxel

In the above representative example of the acid labile molecular conjugate of paclitaxel, each of the -ALL$^1$ and -ALL$^2$ is independently hydrogen or an -ALL group as defined herein. For HBCCA groups having more than one hydroxyl groups, the inaccessible hydroxyl group or groups where the acid labile lipophilic group cannot be formed, then the group that is designated as an -ALL group(s) is hydrogen.

In another embodiment, there is provided a method of producing acid labile, lipophilic molecular conjugates for use in treatment of cancer patients. In one aspect, the method comprises a trans-ketalization of solketal (2,2-dimethyl-4-hydroxymethyl-1,3-dioxolane) with an aldehyde or a ketone to form a compound of formula 4. Compound 4 may be condensed with an acid halide (where X is a halide) to form the compound of formula 3. In one variation of the compound of the formula 3, the p-nitrophenoxy group may be replaced by a leaving group such as a 2-halo-phenoxy, 2,4-halo-phenoxy, 2,4,6-trihalo-phenoxy, 2,6-dihalo-phenoxy, wherein halo is selected from the group consisting of fluoro, chloro, bromo or iodo.

Condensation of 3 with a HBCCA (R—OH) provides the acid labile, lipophilic molecular conjugate of the cancer chemotherapeutic compound 1, wherein R, R$^1$ and R$^2$ are as defined herein.

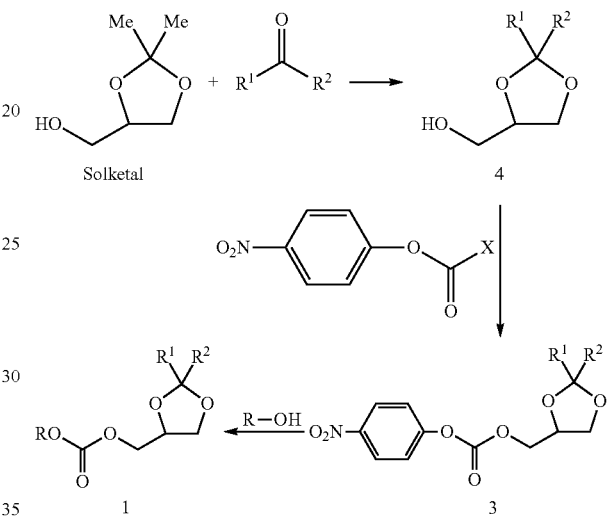

In another embodiment there is provided a method of preparing a compound of the formula 2a comprising a condensation reaction of a HBCCA with an enol ether or vinyl ether to form a compound of the formula 2a:

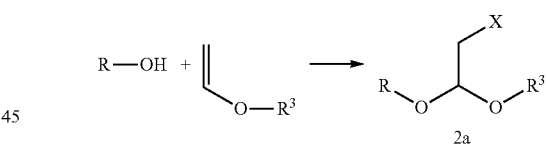

wherein R—OH is the HBCCA, R$^3$ is a $C_2$-$C_{23}$ alkyl, and X is hydrogen or a halogen selected from Cl, Br or I.

In another embodiment, there is provided a method for concentrating a cancer chemotherapeutic agent in selected target cells of a patient using the acid labile, lipophilic molecular conjugates of the present application in a nanoparticulate lipid emulsion resembling a LDL particles or "pseudo-LDL particles". In another embodiment, the method comprises administering to a patient a selected dose of a therapeutically effective amount of the acid labile, lipophilic molecular conjugate of a cancer chemotherapeutic agent dissolved in the lipid core of the pseudo-LDL particles.

Also included in the above embodiments, aspects and variations are salts of amino acids such as arginate and the like, gluconate, and galacturonate. Some of the compounds of the invention may form inner salts or Zwitterions. Certain of the compounds of the present invention can exist in unsolvated forms as well as solvated forms, including hydrated forms, and are intended to be within the scope of the present invention. Certain of the above compounds may also exist in one or more solid or crystalline phases or polymorphs, the variable biological activities of such polymorphs or mixtures of such polymorphs are also included in the scope of this invention. Also provided are pharmaceutical compositions comprising pharmaceutically acceptable excipients and a therapeutically effective amount of at least one compound of this invention.

Pharmaceutical compositions of the compounds of this invention, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, 5% dextrose in water or buffered sodium or ammonium acetate solution. Such formulations are especially suitable for parenteral administration but may also be used for oral administration. Excipients, such as polyvinylpyrrolidinone, gelatin, hydroxycellulose, acacia, polyethylene glycol, mannitol, sodium chloride, or sodium citrate, may also be added. Alternatively, these compounds may be encapsulated, tableted, or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols or water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulation, and compressing, when necessary, for tablet forms; or milling, mixing, and filling for hard gelatin capsule forms. When a liquid carrier is used, the preparation will be in the form of a syrup, elixir, emulsion, or an aqueous or nonaqueous suspension. Such a liquid formulation may be administered directly p.o. or filled into a soft gelatin capsule. Suitable formulations for each of these methods of administration may be found in, for example, *Remington: The Science and Practice of Pharmacy*, A. Gennaro, ed., 20th edition, Lippincott, Williams & Wilkins, Philadelphia, Pa.

These and other objects of the present invention will become more readily appreciated and understood from a consideration of the following detailed description of the exemplary embodiments of the present invention when taken together with the accompanying drawings and figures. The entire disclosures of all documents cited throughout this application are incorporated herein by reference.

BRIEF DESCRIPTION OF THE FIGURES

FIG. 1 depicts a graph of the stability of ART 273 when added to mouse plasma.

FIG. 2 depicts a graph of the stability of ART 273 when added to rat plasma.

FIG. 3 depicts a graph of the stability of ART 273 when added to human plasma.

FIG. 4 depicts a graph of the stability of ART 488 when added to mouse plasma.

FIG. 5 depicts a graph of the stability of ART 488 when added to rat plasma.

FIG. 6 depicts a graph of the stability of ART 488 when added to human plasma.

FIG. 7 depicts a graph of the stability of ART 488 in Liposyn® when added to mouse plasma.

FIG. 8 depicts a graph of the stability of ART 488 in Liposyn® when added to human plasma.

FIG. 9 depicts a graph of the stability of ART 198 when added to mouse plasma.

FIG. 10 depicts a graph of the stability of ART 198 when added to rat plasma.

FIG. 11 depicts a graph of the stability of ART 198 when added to human plasma.

FIG. 12 depicts a graph of the stability of ART 489 when added to mouse plasma.

FIG. 13 depicts a graph of the stability of ART 489 when added to rat plasma.

FIG. 14 depicts a graph of the stability of ART 489 when added to human plasma.

FIG. 15 depicts a graph of the stability of ART 489 in Liposyn® when added to mouse plasma.

FIG. 16 depicts a graph of the stability of ART 489 in Liposyn® when added to human plasma.

FIG. 17 depicts a graph of the stability of ART 467 when added to human plasma.

FIGS. 18, 19 and 20 depict representative acid labile lipophilic molecular conjugates, wherein -ALL1, -ALL2, -ALL3 and -ALL4 are each independently hydrogen or an acid labile lipophilic group, provided that at least one of -ALL1, -ALL2, -ALL3 and -ALL4 is an acid labile lipophilic group.

DETAILED DESCRIPTION OF THE EXEMPLARY EMBODIMENTS

Figure 18:
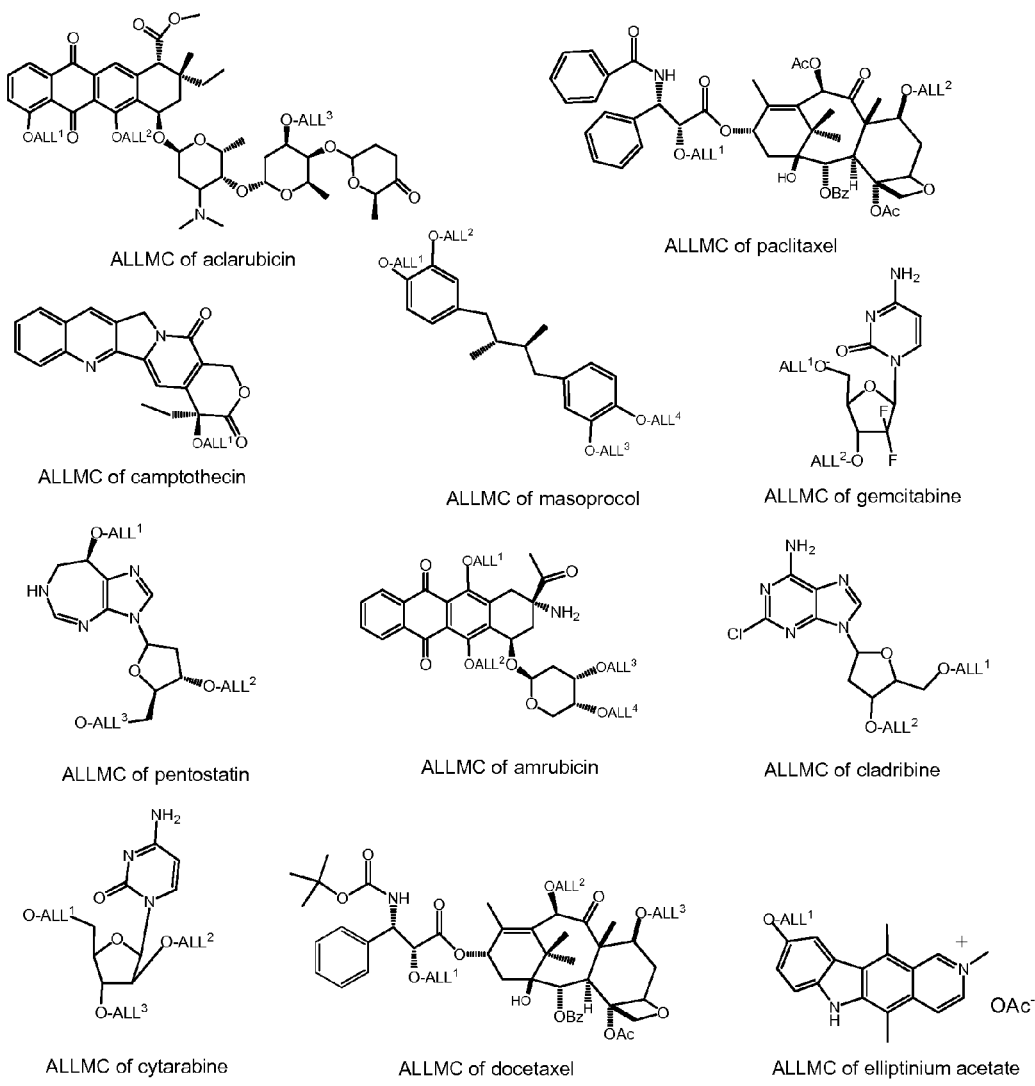

The following procedures may be employed for the preparation of the compounds of the present invention. The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In some cases, protective groups may be introduced and finally removed. Suitable protective groups for amino, hydroxy, and carboxy groups are described in Greene et al., *Protective Groups in Organic Synthesis*, Second Edition, John Wiley and Sons, New York, 1991. Standard organic chemical reactions can be achieved by using a number of different reagents, for examples, as described in Larock: *Comprehensive Organic Transformations*, VCH Publishers, New York, 1989.

General Procedure for Synthesis of Acid Labile, Lipophilic Molecular Conjugates of Cancer Chemotherapeutic Agents. Formation of Activated Intermediate Compounds:

Compounds suitable for use for forming acid labile, lipophilic molecular conjugates of cancer chemotherapeutic agents may be prepared according to the general methods disclosed herein. In one aspect, solketal is reacted with an alkyl aldehyde or a dialkyl ketone in the presence of acid catalysis and an organic solvent to form the aldehyde solketal (acetal) derivative or the ketone solketal (ketal) derivative, respectively. According to the present method, 5-membered and 6-membered cyclic acetals may be prepared and may be isolated in substantially pure form by chromatography. In one aspect, the solvent is toluene and the reaction is performed at an elevated temperature, such as about 60 to 80° C. The acetal or ketal solketal derivative is subsequently activated by a reaction with an acid halide, such as 4-nitrophenyl chloroformate in the presence of base catalysis to form the corresponding activated derivative, such as the 4-nitrophenyl carbonate intermediate compound of the formula 3. In one aspect, the 4-nitrophenyl carbonate intermediate may be condensed with a HBCCA to form the acid labile, lipophilic molecular conjugate.

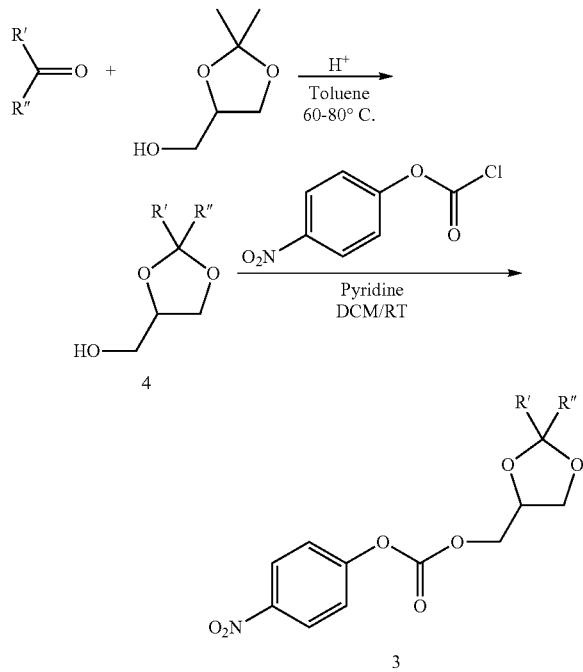

In another aspect solketal is first reacted with an acid halide such as 4-nitrophenyl chloroformate in the presence of base catalysis to form solketal nitrocarbonate which is subsequently reacted with an alkyl aldehyde or a dialkyl ketone in the presence of acid catalysis and an organic solvent to form the aldehyde solketal (acetal) derivative or the ketone solketal (ketal) derivative of formula 3, respectively. In one aspect, the solvent is toluene and the reaction is performed at RT. In one aspect, the 4-nitrophenyl carbonate intermediate may be condensed with a HBCCA to form the corresponding acid labile, lipophilic molecular conjugate.

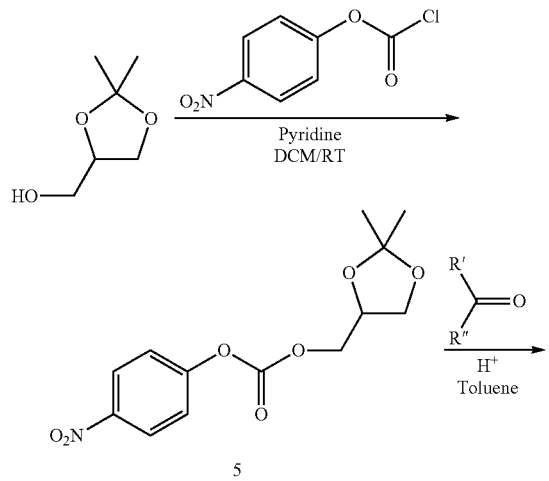

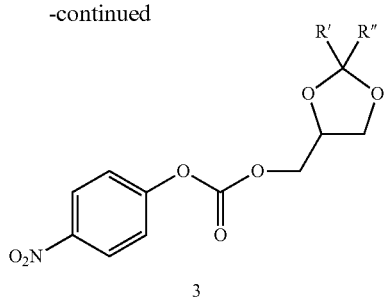

In another aspect alcohol such as stearyl alcohol is reacted with vinyl acetate in the presence of a transition metal catalyst such as $[Ir(cod)Cl]_2$ and a base additive such as $Na_2CO_3$ to form the corresponding vinyl ether. In one aspect, the solvent is toluene and the reaction is performed at 100° C. In one aspect, the vinyl ether derivative may be condenced with a HBCCA to form the corresponding acid labile, lipophilic molecular conjugate.

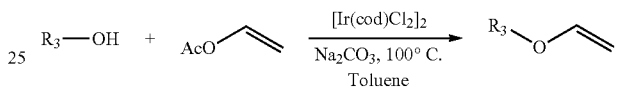

General Procedure for Synthesis of Alternative Acid Labile, Lipophilic Molecular Conjugates of Cancer Chemotherapeutic Agents:

In one embodiment, the HBCCA may be reacted with the 4-nitrophenyl carbonate compound in the presence of a base, such as a catalytic amount of N,N-dimethyl-4-aminopyridine (DMAP) and pyridine, in an organic solvent, such as dichloromethane (DCM) at room temperature (RT), to form the desired acid labile, lipophilic molecular conjugate.

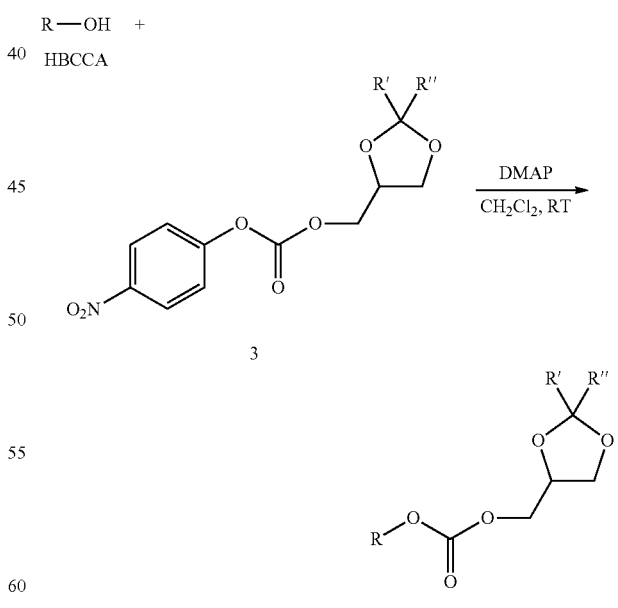

As shown in the scheme below, initial synthesis of activated acid labile, lipophilic molecular conjugate intermediates have been obtained by treating solketal with the aldehyde derived from the corresponding natural fatty acid followed by reaction with 4-nitrophenyl chloroformate.

Scheme: Synthesis of lipophilic carbonate molecular conjugate intermediates: Early approach

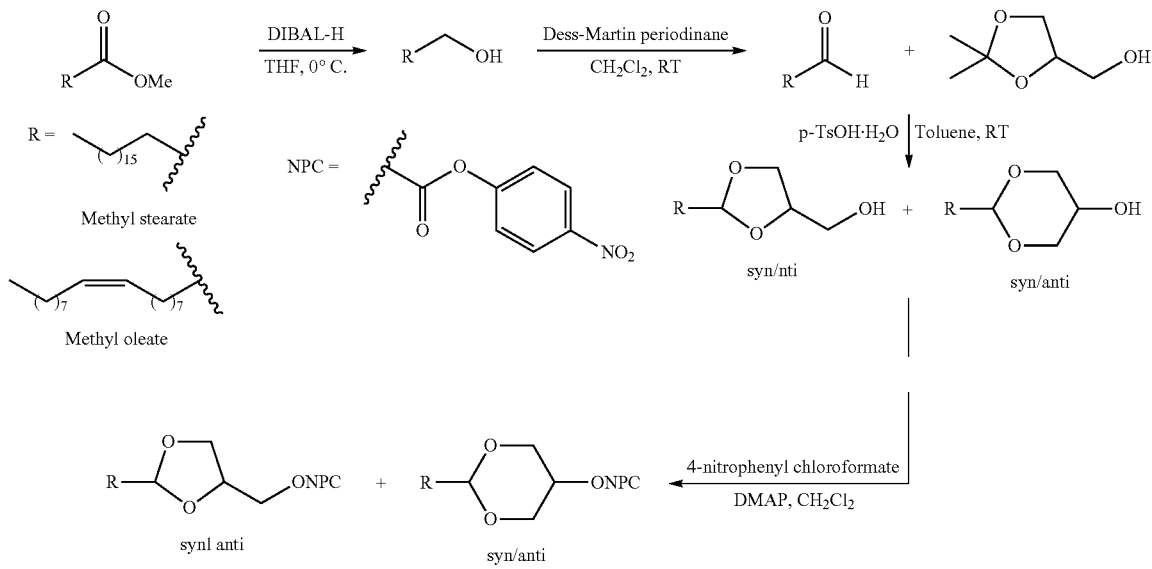

However, this method result the formation of 5- and 6 membered conjugates along with their corresponding syn/anti isomers. Although both 5- and 6-membered acetals could act as lipophilic conjugate precursors, 3 sets of regio- and stereo isomers were isolated in the acetal formation step. In one embodiment, the desired acetal may be isolated in substantially pure form by chromatography. An alternate reaction sequence for the preparation of the 5-membered acetal is shown below. This route provides the 5-membered acetal and provides a method to access lipophilic conjugates of various candidate chemotherapeutic agents. The activated carbonate intermediate is further treated with the hydroxyl-bearing cancer chemotherapeutic agents to generate the corresponding acid labile, lipophilic molecular conjugate prodrugs of interest.

Scheme: Synthesis of lipophilic carbonate molecular conjugate intermediates and prodrugs: Modified approach

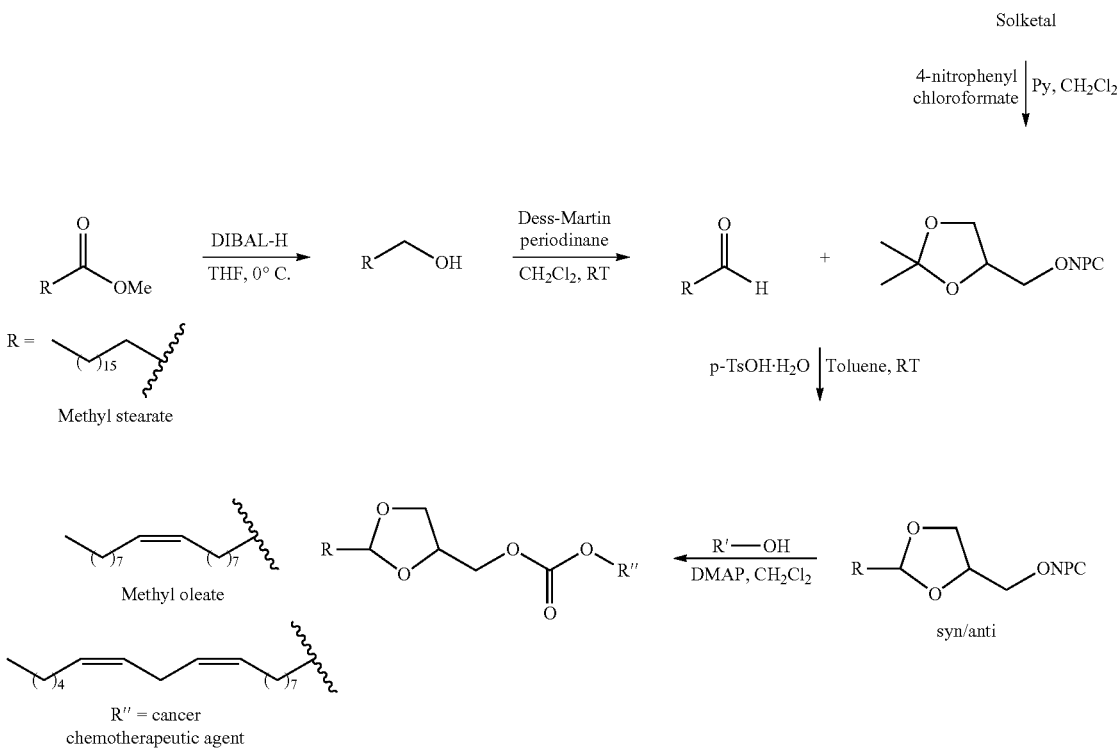

Alternative acid labile, lipophilic molecular conjugates of cancer chemotherapeutic agents may be formed by reacting a HBCCA with an alkyl vinyl ether in the presence of a halogenating agent, such as an NXS, such as N-bromosuccinimide (NBS) in DCM. In one aspect, the reactants are combined in solution at low temperatures, such as about −78° C., and the reaction is stirred and allowed to warm slowly to RT.

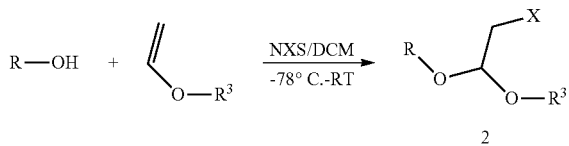

2

Other alternative acid labile, lipophilic molecular conjugates of cancer chemotherapeutic agents may be formed by reacting HBCCA with higher alkyl vinyl ethers (derived from natural fatty acids) in the presence of an acid catalyst such as pyridinium para-toluene sulfonate (PPTS). In one aspect, the reactants are combined in solution at RT to synthesize the corresponding acid labile lipophilic acetal prodrug.

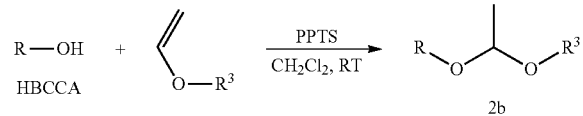

2b

Formation of Acid-Labile Lipophilic Conjugates:

Method A: A solution of the 4-nitrophenyl carbonate-solketal conjugate of formula 3 (0.21 mmol) in anhydrous (anh.) dichloromethane (1 ml) was added to a solution of HBCCA (0.2 mmol) and DMAP (0.3 mmol) in anh. dichloromethane (2 ml) and the reaction mixture was stirred at RT under nitrogen atmosphere ($N_2$). The reaction progress was monitored by TLC/HPLC, upon completion, the reaction mixture was diluted with methylene chloride (DCM), washed with $NH_4Cl$(s), water and brine. The organic layer was separated, dried over sodium sulfate and evaporated. The crude residue was purified by silica gel flash chromatography (SGFC) to obtain the conjugated prodrug.

Method B: To a solution of alkyl vinyl ether (1.2 mmol, 6 eq.) and HBCCA (0.2 mmol, 1 eq.) in anh. DCM (8 mL, 0.025M), NBS (1 mmol, 5 eq.) was added at −15° C. under $N_2$. The reaction mixture was stirred at −15° C. to 0° C. and the progress of the reaction was monitored by TLC/HPLC. Upon completion, the reaction mixture was diluted with DCM and the reaction mixture was washed with $NaHCO_3$ (sat.), water and brine solution. Organic layer was dried over sodium sulfate and evaporated. The crude residue was purified by SGFC to yield the conjugated prodrug.

Method C: To a solution of alkyl vinyl ether (1.2 mmol, 6 eq.) and HBCCA (0.2 mmol, 1 eq.) in anh. DCM (8 mL, 0.025M), PPTS (0.02 mmol, 10 mol %) was added and the reaction mixture was stirred at RT under $N_2$. The reaction progress was monitored by TLC/HPLC. Upon completion, the reaction mixture was diluted with DCM and the reaction mixture was washed with $NaHCO_3$(sat.), water and brine solution. Organic layer was dried over sodium sulfate and evaporated. The crude residue was purified by SGFC to yield the conjugated prodrug.

Characterization of Acid Labile Lipophilic Conjugates:

Acid labile lipophilic conjugates were characterized by a combination of HPLC and High Resolution Mass Spectrometry. Specifics are provided with each compound.

Preparation of ART 449

A solution of the 4-nitrophenyl carbonate of docosahexaenoic alcohol (0.5 g) in anh DCM was added to a solution of ART 273 (0.522 g) and DMAP (0.140 g) in anh DCM (18 mL) at RT under $N_2$ and stirred. Upon completion, the reaction was diluted with DCM, washed with saturated ammonium chloride solution ($NH_4Cl$(s)), water and brine. The organic layer was separated, dried over sodium sulfate and evaporated. The crude residue was purified over silica gel to yield ART 449 as a white solid. −TOF MS: m/z 1003.4859 $(M+CF_3CO_2)^-$

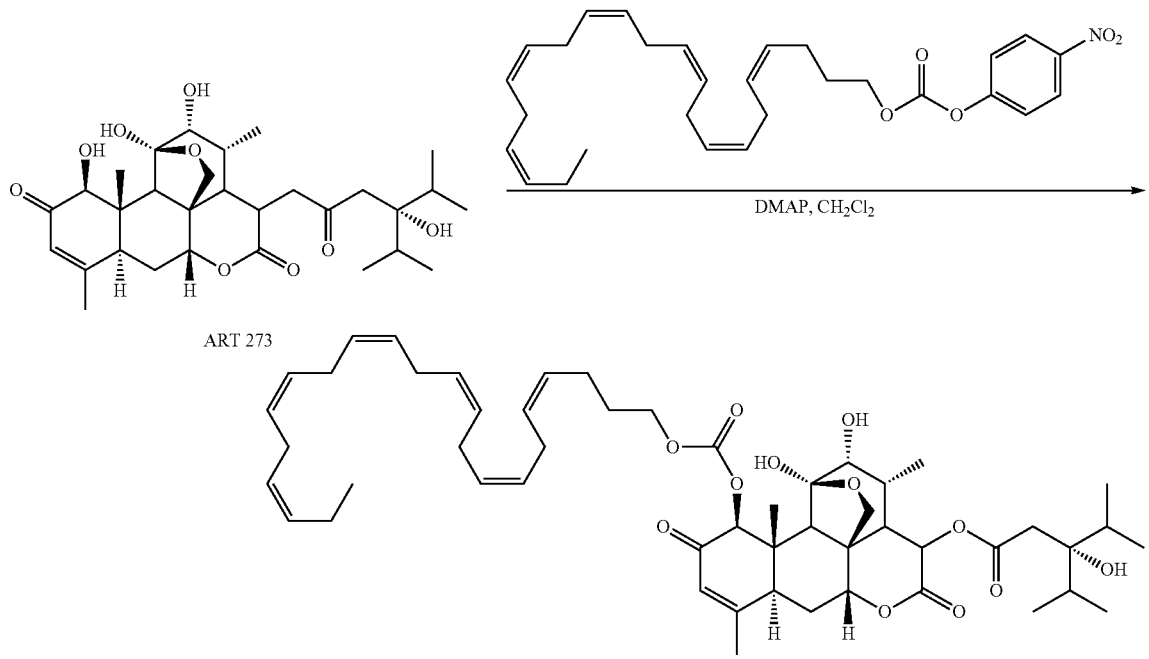

Preparation of ART 448

A solution of the 4-nitrophenyl carbonate of 5-hexen-1-ol (0.1 g) in anh. DCM was added to a solution of ART 273 (0.207 g) and DMAP (0.051 g) in anh DCM (5 mL) at RT under N$_2$. Upon completion, the reaction was diluted with DCM, washed with NH$_4$Cl(s), water and brine. The organic layer was separated, dried over sodium sulfate and evaporated. The crude residue was purified over silica gel to yield ART 448 as a white solid. −TOF MS: m/z 789.2928 (M+CF$_3$CO$_2$)$^−$

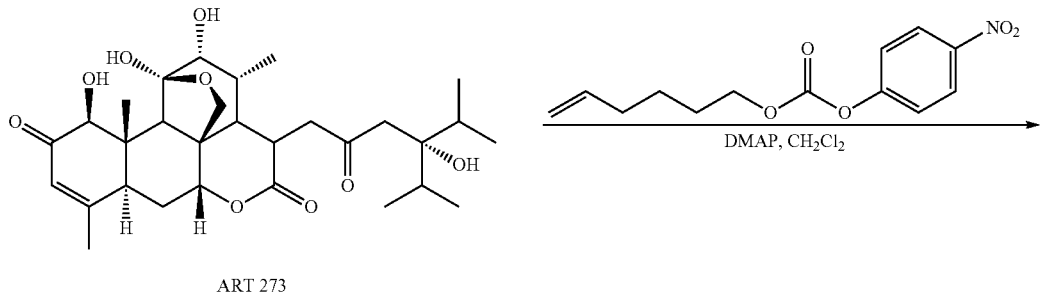

ART 273

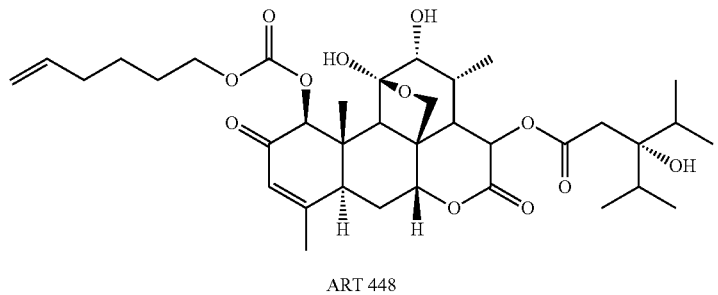

ART 448

Preparation of ART 473

Cyclohexyl vinyl ether (0.24 mL) was added to a solution of ART 273 (0.230 g) and NBS (0.282 g) in anh DCM (5 mL) at −78° C. under N$_2$. Upon completion, the solution was evaporated and the crude residue purified over silica gel to yield ART 473 as a white solid.

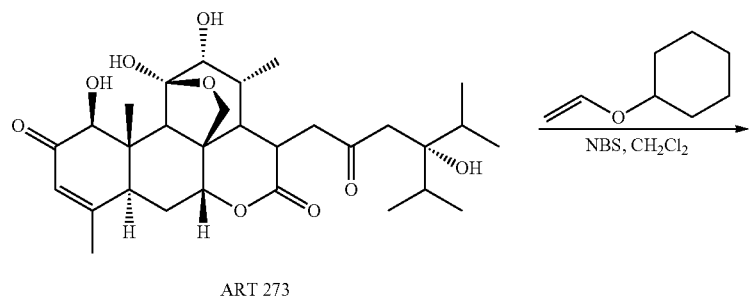

ART 273

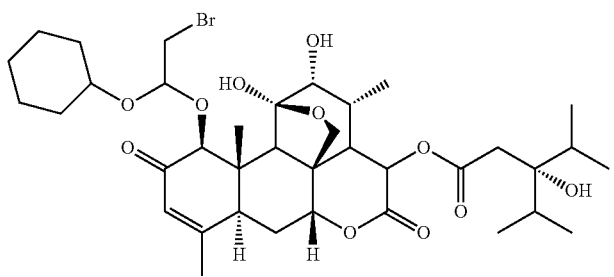

ART 473

Preparation of ART 471

Tert-Butyl vinyl ether (0.24 mL) was added to a solution of ART 273 (0.250 g) and NBS (0.307 g) in anh DCM (5 mL) at −78° C. under N₂. Upon completion, the solution was evaporated and the crude residue purified over silica gel to yield ART 471 as a white solid.

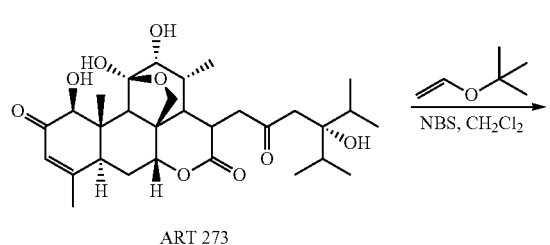

ART 273

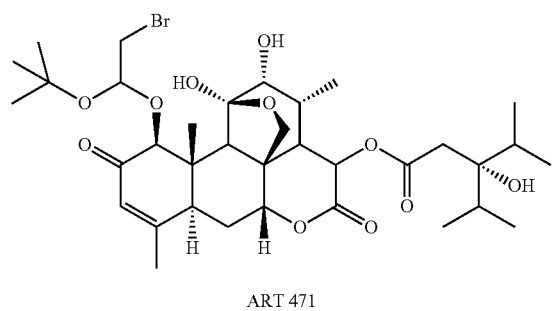

ART 471

Preparation of ART 472

Octadecyl vinyl ether (0.448 g) was added to a solution of ART 273 (0.208 g) and NBS (0.255 g) in anh DCM (5 mL) at −78° C. under N₂. Upon completion, the solution was evaporated and the crude residue purified over silica gel to yield ART 472 as a white solid.

Preparation of ART 470

Ethyl vinyl ether (0.11 mL) was added to a solution of ART 273 (0.150 g) and N-bromosuccinimide (NBS, 0.170 g) in anh. DCM (5 mL) at −78° C. under N₂. Upon completion, the solution was evaporated and the crude residue purified over silica gel to yield ART 470 as a white solid.

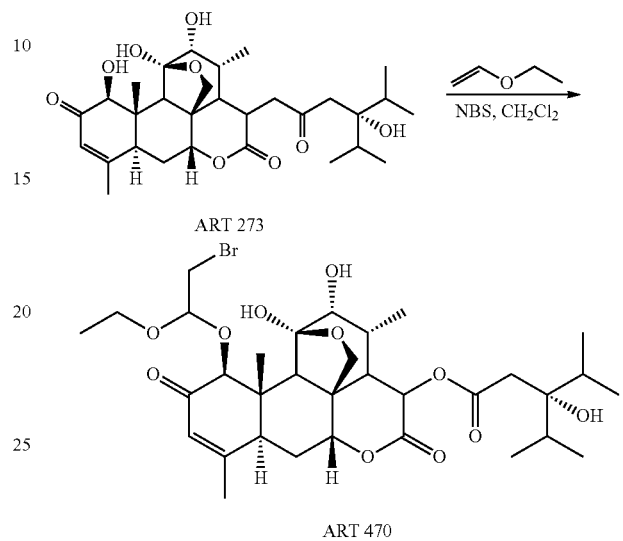

ART 273

ART 470

Preparation of ART 489

A solution of octadecyl solketal-4-nitrophenyl carbonate (0.750 g) in anh. DCM was added to a solution of ART 198 (0.754 g) and DMAP (0.238 g) in anh DCM (30 mL) at RT under N₂. Upon completion, the reaction was diluted with DCM, washed with NH₄Cl(s), water and brine. The organic layer was separated, dried over sodium sulfate and evaporated. The crude residue was purified over silica gel to yield ART 489 as a solid. −TOF MS: m/z 1031.4645 (M+CF₃CO₂)⁻

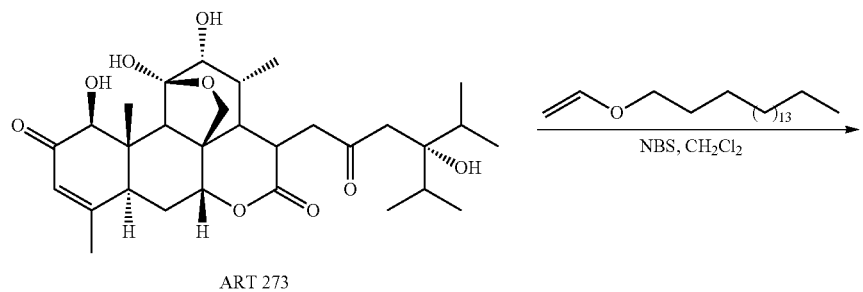

ART 273

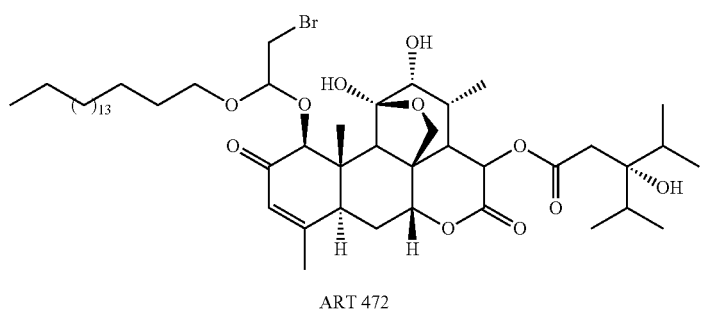

ART 472

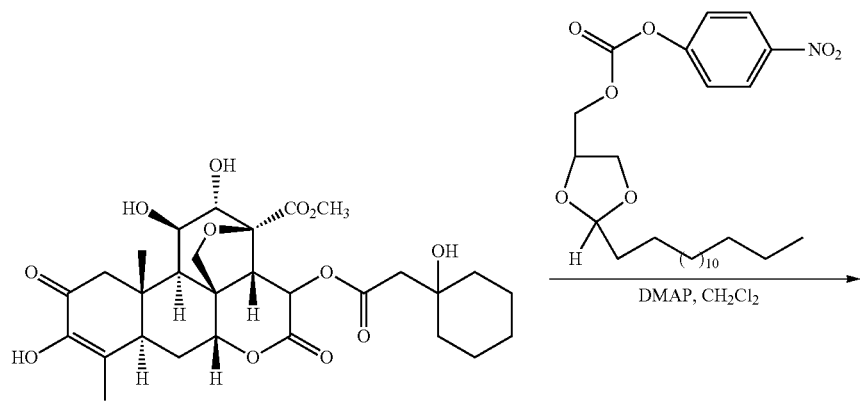

ART 198

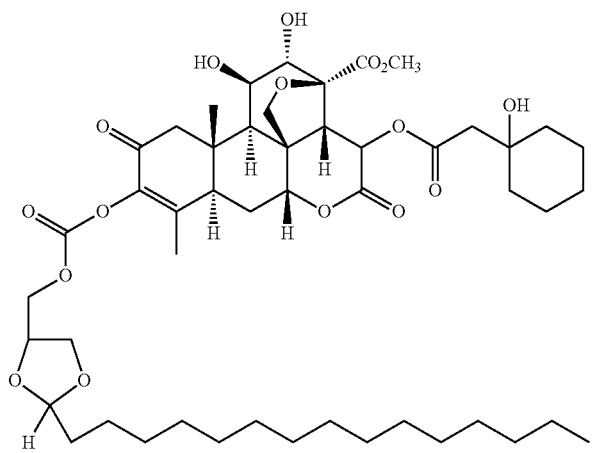

ART 489

Preparation of ART 488

A solution of octadecyl solketal-4-nitrophenyl carbonate (0.53 g) in anh DCM was added to a solution of ART 273 (0.507 g) and DMAP (0.168 g) in anh DCM (30 mL) at RT under $N_2$. Upon completion, the reaction was diluted with DCM, washed with $NH_4Cl(s)$, water and brine. The organic layer was separated, dried over sodium sulfate and evaporated. The crude residue was purified over silica gel to yield ART 488 as a solid. −TOF MS: m/z 1003 4994 $(M+CF_3CO_2)^-$

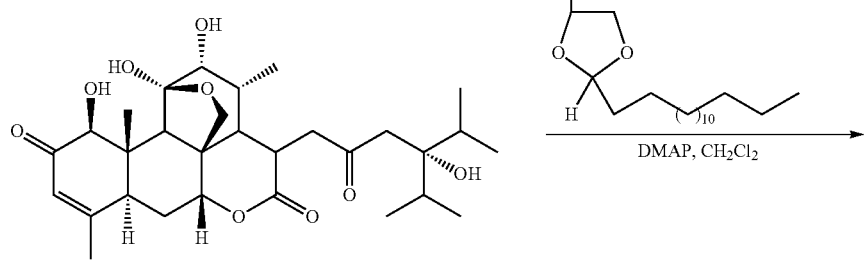

ART 273

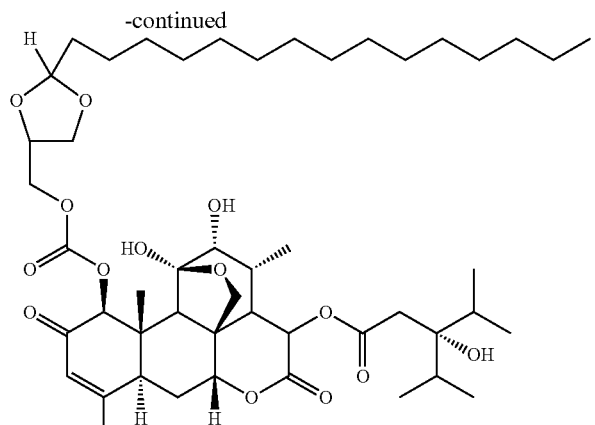

ART 488

Preparation of ART 332

A solution of solketal-4-nitrophenyl carbonate (1.1 g) in anh. DCM was added to a solution of ART 273 (1.30 g) and DMAP (0.36 g) in anh DCM (30 mL) at RT under $N_2$. Upon completion, the reaction was diluted with DCM, washed with $NH_4Cl(s)$, water and brine. The organic layer was separated, dried over sodium sulfate and evaporated. The crude residue was purified over silica gel to yield ART 332 as a white solid. −TOF MS: m/z 947.4601 $(M+CF_3CO_2)^−$

Preparation of ART 441

DHA (0.2 g), DCC (0.157 g) and DMAP (0.006 g) were sequentially added to a solution of ART 273 (0.279 g) in anh. DCM (10 mL) at RT under $N_2$. Upon completion, the reaction was diluted with DCM, washed with $NH_4Cl(s)$, water and brine. The organic layer was separated, dried over sodium sulfate and evaporated. The crude residue was purified over silica gel to yield ART 441 (0.2 g) as a white solid.

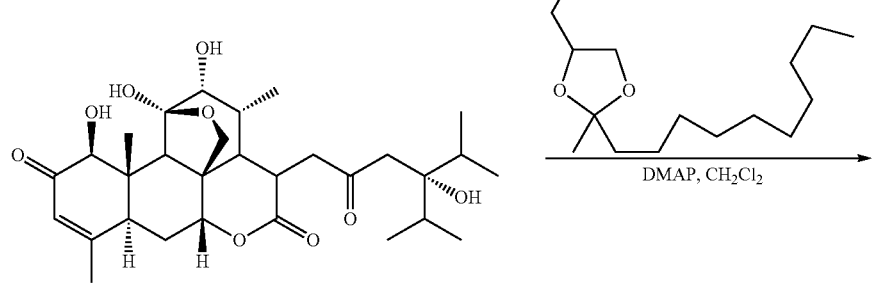

ART 273

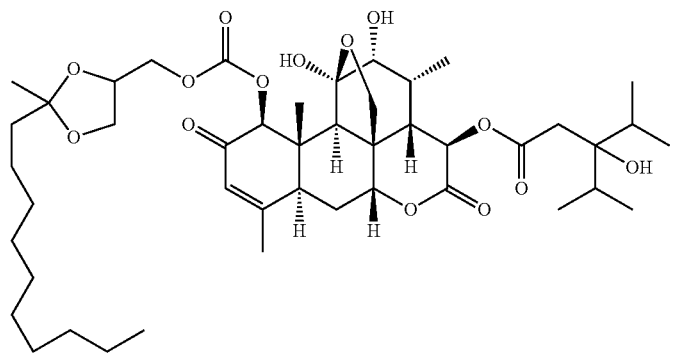

ART 332

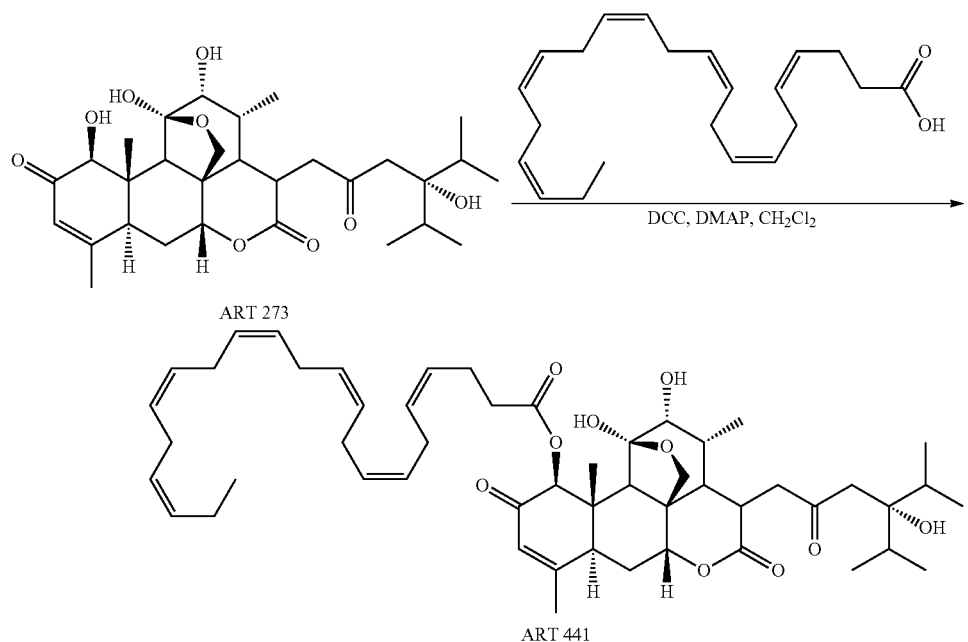

Preparation of ART 467

A solution of octadecyl solketal-4-nitrophenyl carbonate (1.75 g) in anh DCM was added to a solution of paclitaxel (2.59 g) and DMAP (0.557 g) in anh DCM (30 mL) at RT under $N_2$. Upon completion, the reaction was diluted with DCM, washed with $NH_4Cl(s)$, water and brine. The organic layer was separated, dried over sodium sulfate and evaporated. The crude residue was purified over silica gel to yield ART 467 as a white solid. –TOF MS: m/z 1306.5445 $(M+CF_3CO_2)^-$

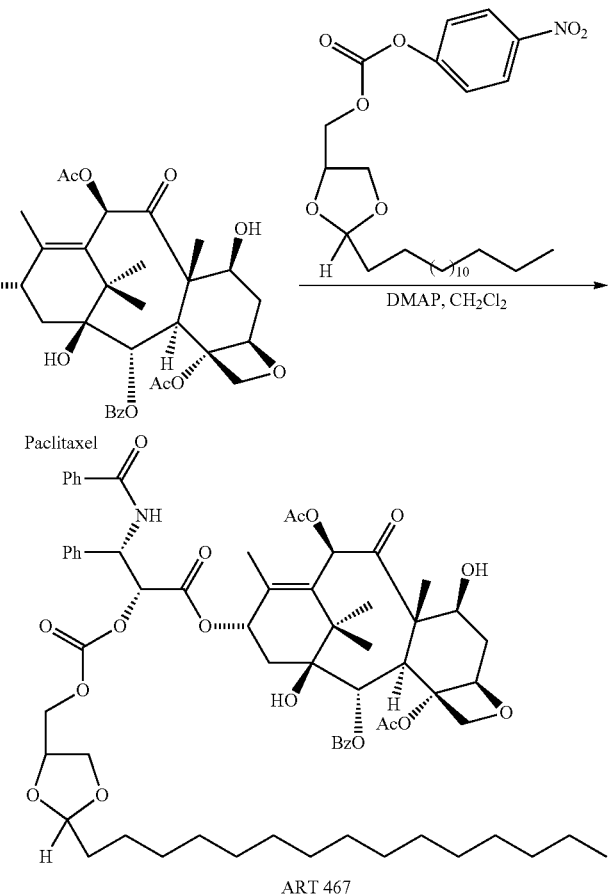

Preparation of ART 151

ART 151 was prepared by following the procedure as outlined in Method A. HPLC retention time 6.06, Method: Taxane conjugates_MKG4 (C18 column, MeOH/H₂O/THF 95/3/2 to 100% MeOH 10 min, 2 min 100% MeOH, 230 nm, 1.5 ml/min, 30° C., 14 min). +TOF MS: m/z 1239.6523 [M+18] (M+NH$_4^+$)

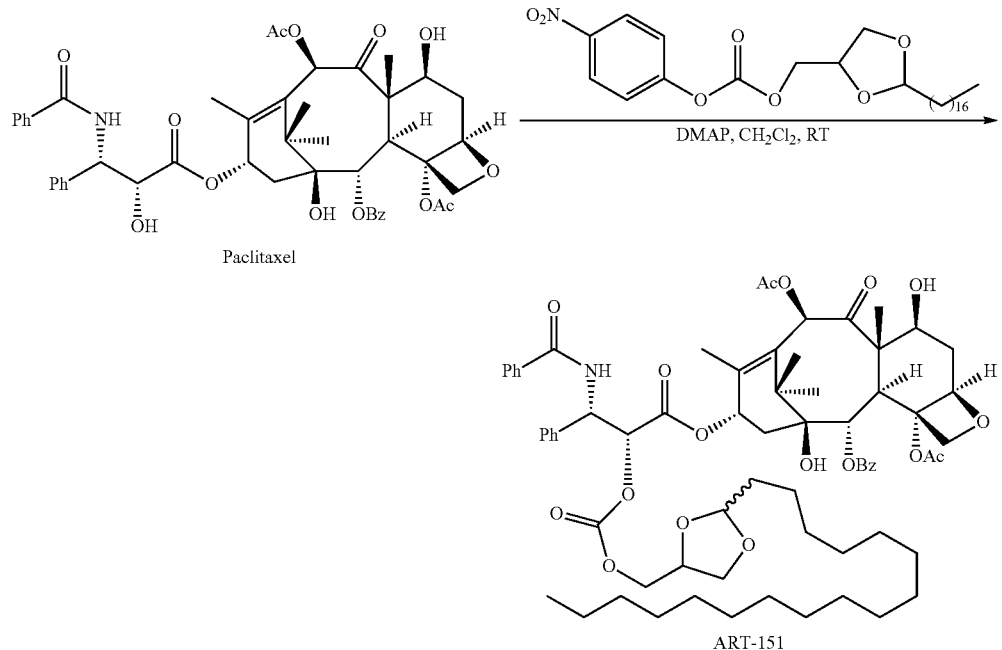

Preparation of ART 152

ART 152 was prepared by following the procedure as outlined in Method B. HPLC retention time 8.21, Method: Taxane conjugates MKG4 (C18 column, MeOH/H₂O/THF 95/3/2 to 100% MeOH 10 min, 2 min 100% MeOH, 230 nm, 1.5 ml/min, 30° C., 14 min). +TOF MS: m/z 1228.5654 [M+1] (M+H$^+$)

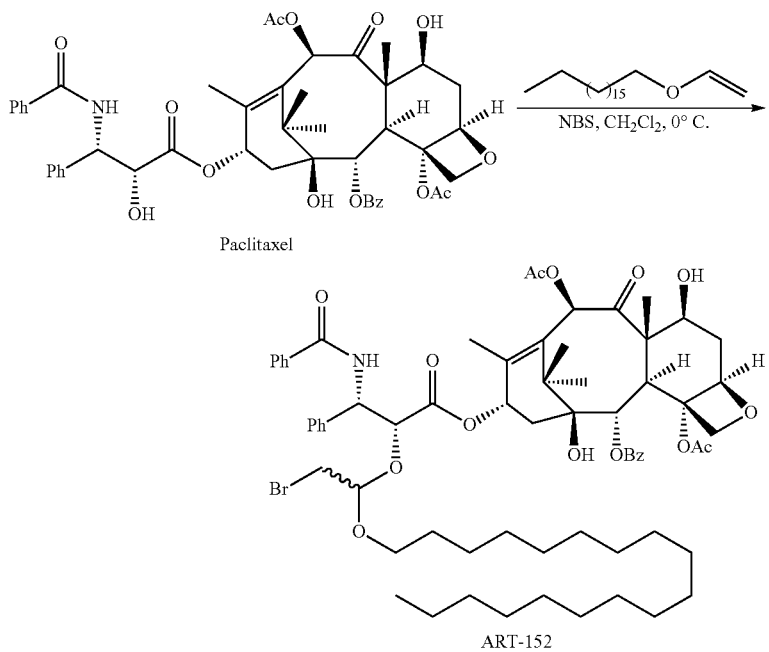

Preparation of ART 153

ART 153 was prepared by following the procedure as outlined in Method C. HPLC retention time 7.05, Method: Taxane conjugates_MKG4 (C18 column, MeOH/H$_2$O/THF 95/3/2 to 100% MeOH 10 min, 2 min 100% MeOH, 230 nm, 1.5 ml/min, 30° C., 14 min). +TOF MS: m/z 1150.6485 [M+1] (M+H$^+$)

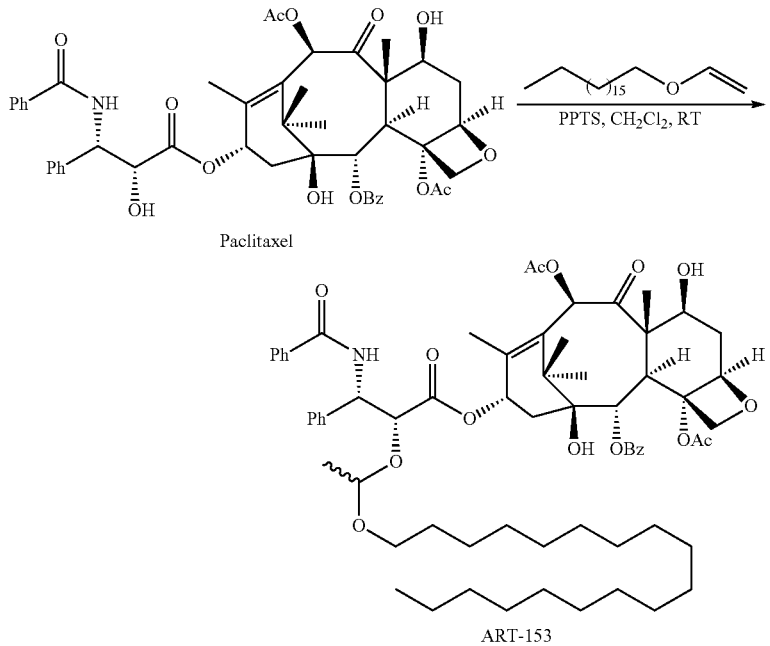

ART 161 was prepared by following the procedure as outlined in Method A. HPLC retention time 4.88, Method: Taxane conjugates_MKG6 (C18 column, MeOH/H$_2$O 95/5 to 100% MeOH 10 min, 2 min 100% MeOH, 230 nm, 1.5 ml/min, 30° C., 16 min). +TOF MS: m/z 1235.6276 [M+18] (M+NH$_4^+$)

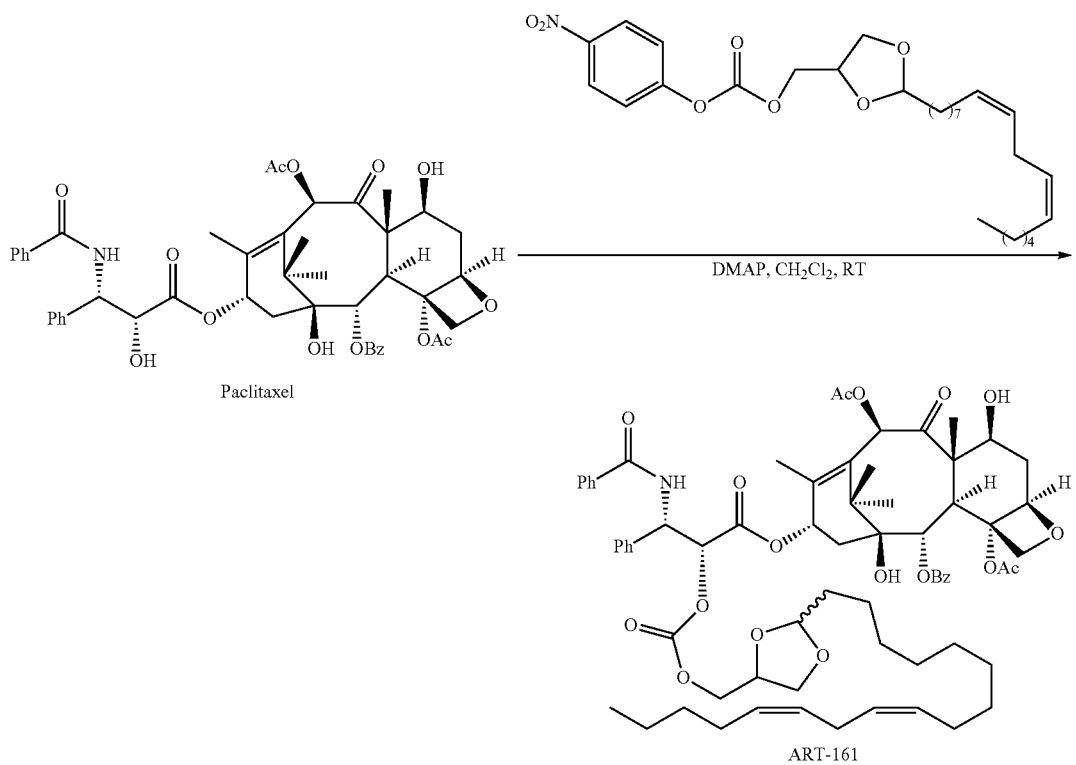

ART 207 was prepared by following the procedure as outlined in Method A. HPLC retention time 6.06, Method; Taxane conjugates_MKG17 (Synergy column, ACN/H$_2$O 60/40 to 100% ACN 10 min, 2 min 100% ACN, 230 nm, 1.5 ml/min, 30° C., 15 min). +TOF MS: m/z 1220.6156 [M+1] and m/z 1237.6382 [M+18] (M+NH$_4^+$)

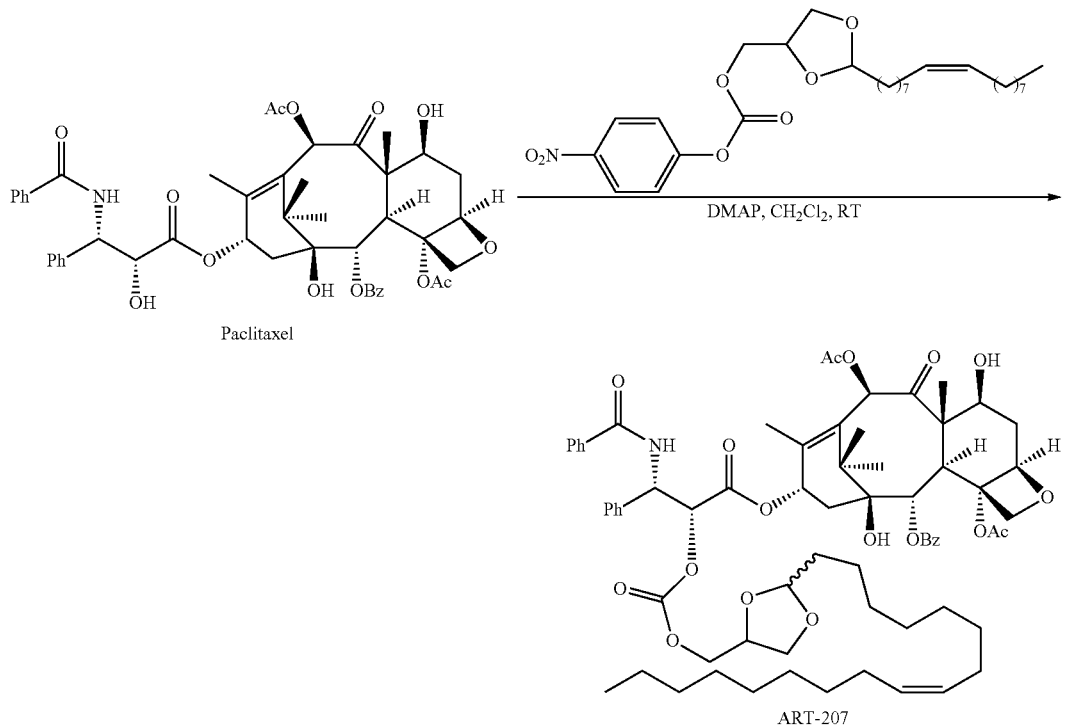

ART 156 was prepared by following the procedure as outlined in Method A. HPLC retention time 6.2, Method: Taxane conjugates_MKG4 (C18 column, MeOH/H$_2$O/THF 95/3/2 to 100% MeOH 10 min, 2 min 100% MeOH, 230 nm, 1.5 ml/min, 30° C., 14 min). +TOF MS: m/z 1176.6466 [M+1] and m/z 1193.6730 [M+18] (M+NH$_4^+$)

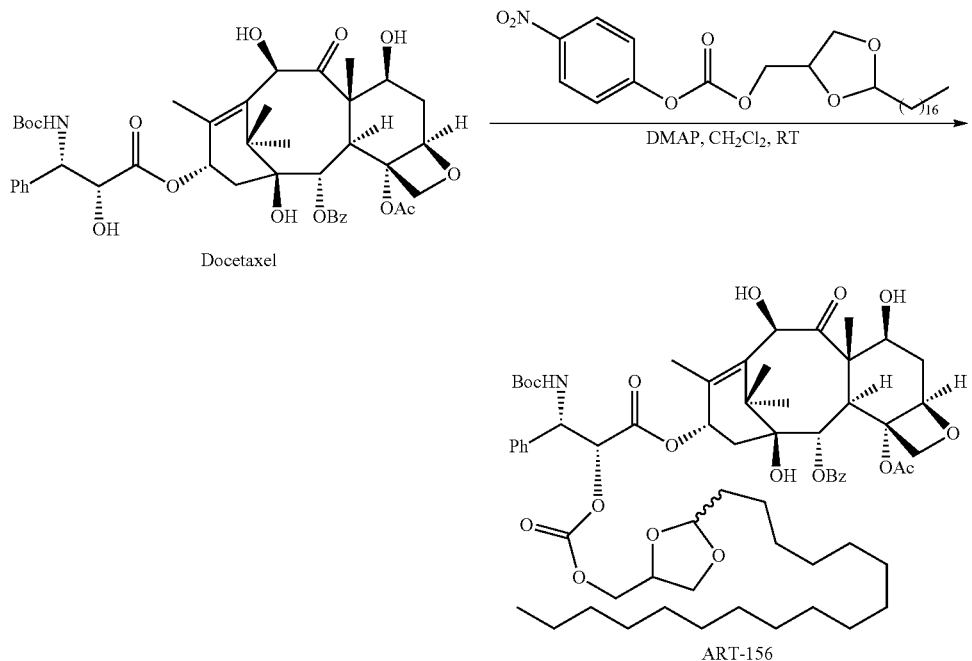

ART 162 was prepared by following the procedure as outlined in Method A. HPLC retention time 8.96, Method: Taxane conjugates_MKG16 (Synergy column, MeOH/H$_2$O 75/25 to 100% MeOH 10 min, 2 min 100% MeOH, 230 nm, 1.5 ml/min, 30° C., 15 min). +TOF MS: m/z 1189.6491 [M+18] and m/z 1172.6224 [M+1] (M+H$^+$)

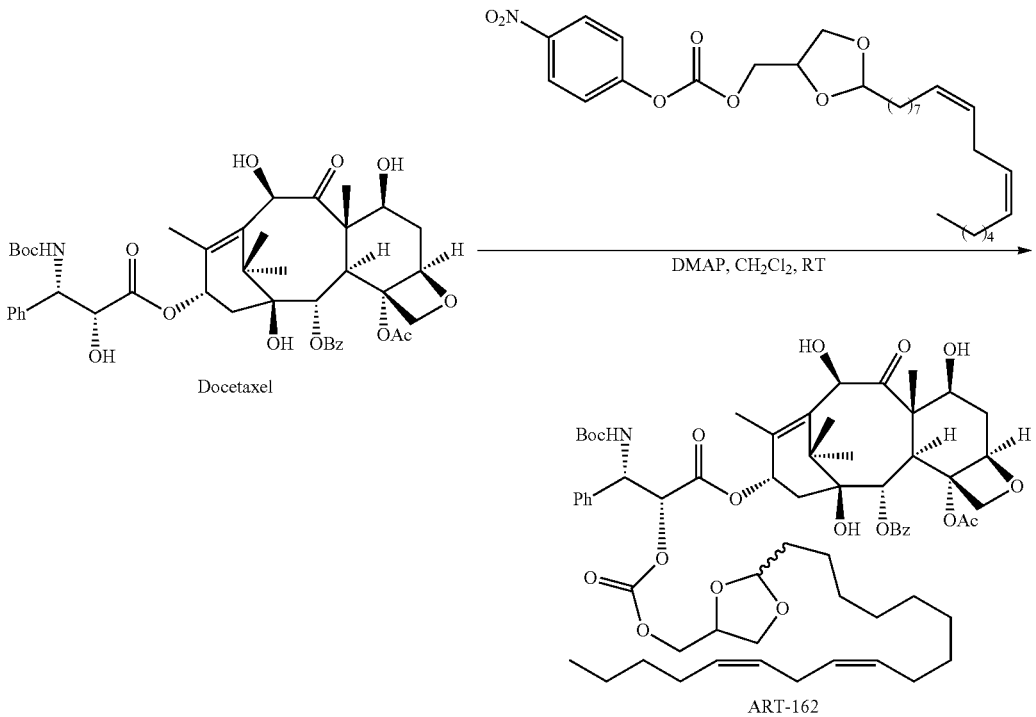

ART 208 was prepared by following the procedure as outlined in Method A. HPLC retention time 7.4, Method: Taxane conjugates_MKG19 (Synergy column, ACN/H$_2$O 50/50 3 min, 80-100% ACN/H$_2$O 10 min, 2 min 100% ACN, 230 nm, 1.5 ml/min, 30° C., 15 min). +TOF MS: m/z 1174.6306 [M+1] (M+H$^+$)

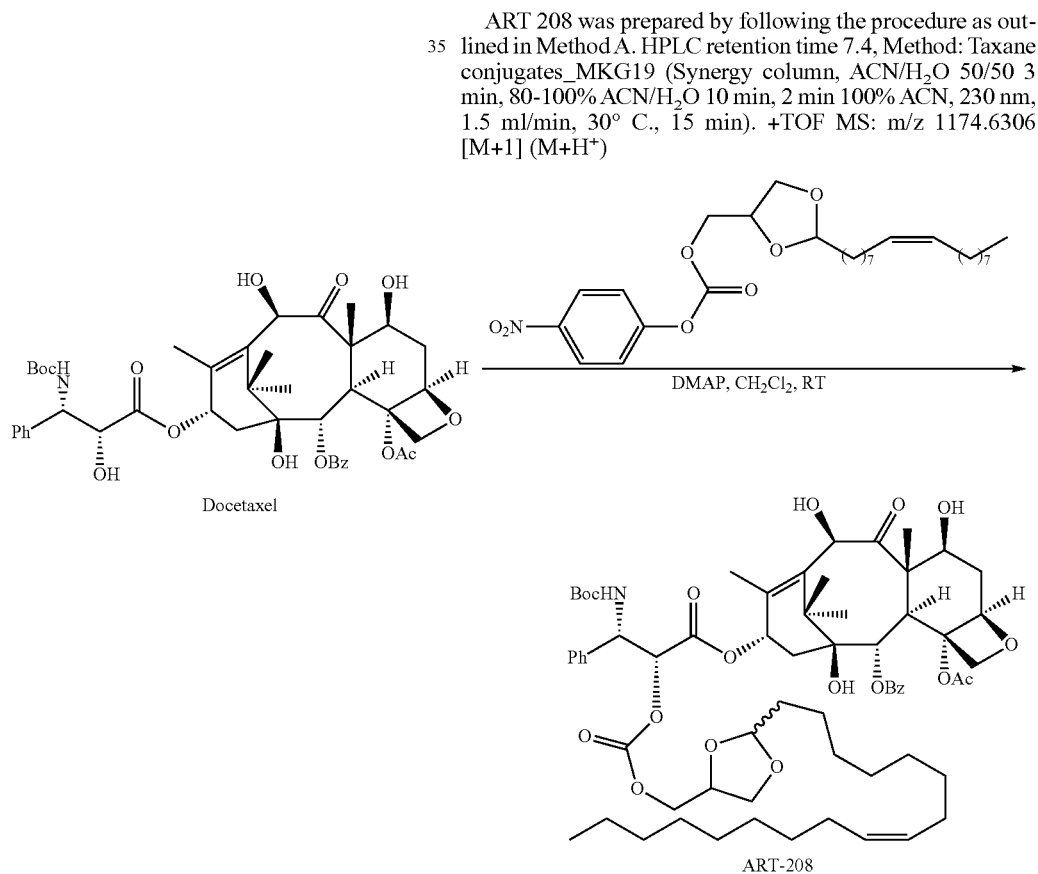

ART 185 was prepared by following the procedure as outlined in Method C. HPLC retention time 6.42, Method: Taxane conjugates MKG15 (Synergy column, 70-100% ACN/H₂O 10 min, 100% ACN 2 min, 230 nm, 1.5 ml/min, 30° C., 15 min). +TOF MS: m/z 1104.6648 [M+1] (M+H⁺) and m/z 1126.6447 [M+18] (M+NH₄⁺)

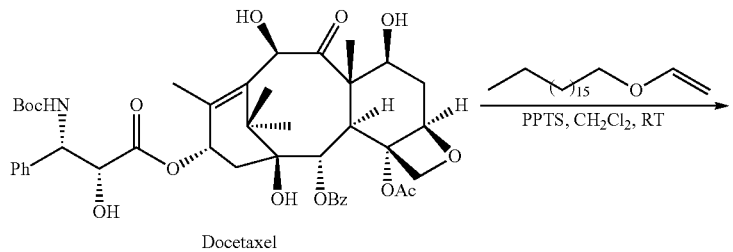

Docetaxel

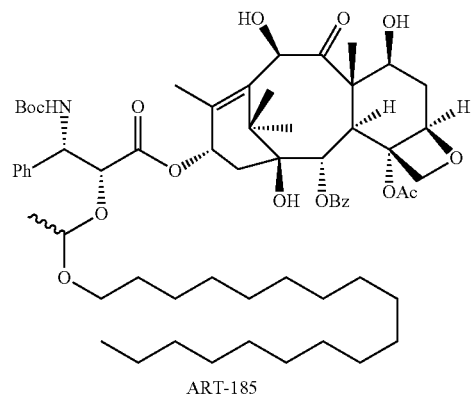

ART-185

ART 137 was prepared by following the procedure as outlined in Method C. HPLC retention time 10.63, Method: Taxane (C18 column, ACN/H₂O 50/50 to 100% ACN 10 min, 2 min 100% ACNH, 230 nm, 1.5 ml/min, 30° C., 16 min)

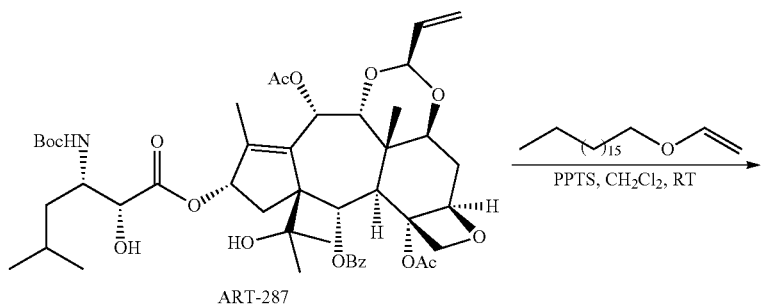

ART-287

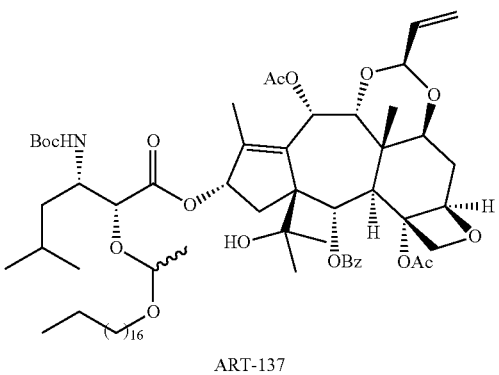

ART-137

ART 164 was prepared by following the procedure as outlined in Method A. HPLC retention time 7.73, Method: Taxane conjugates_MKG6 (C18 column, MeOH/H$_2$O 95/5 to 100% MeOH 10 min, 2 min 100% MeOH, 230 nm, 1.5 ml/min, 30° C., 16 min). +TOF MS: m/z 1255.7506 [M+18] (M+NH$_4^+$)

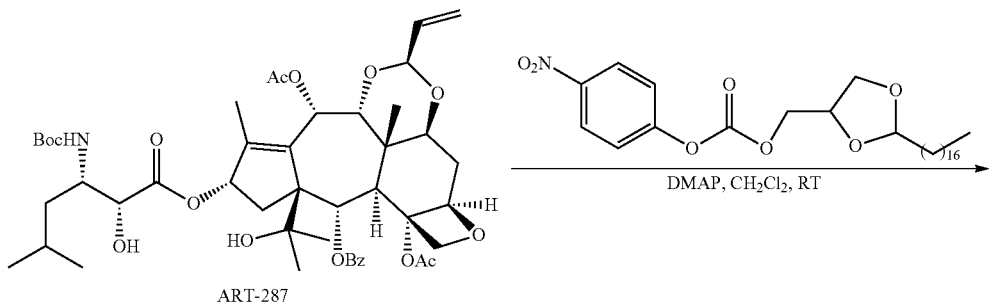

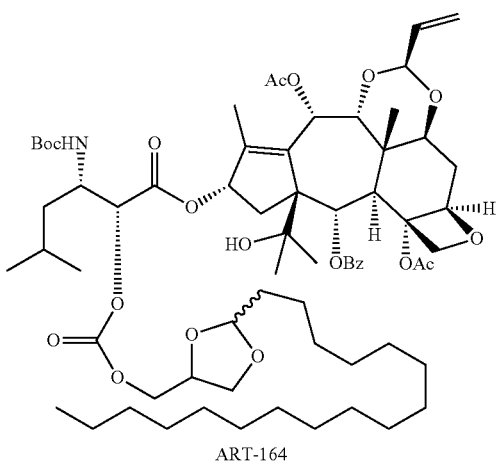

ART 163 was prepared by following the procedure as outlined in Method A. HPLC retention time 7.56, Method: Taxane conjugates_MKG6 (C18 column, MeOH/H$_2$O 95/5 to 100% MeOH 10 min, 2 min 100% MeOH, 230 nm, 1.5 ml/min, 30° C., 16 min). +TOF MS: m/z 1251.7233 [M+18] (M+NH$_4^+$)

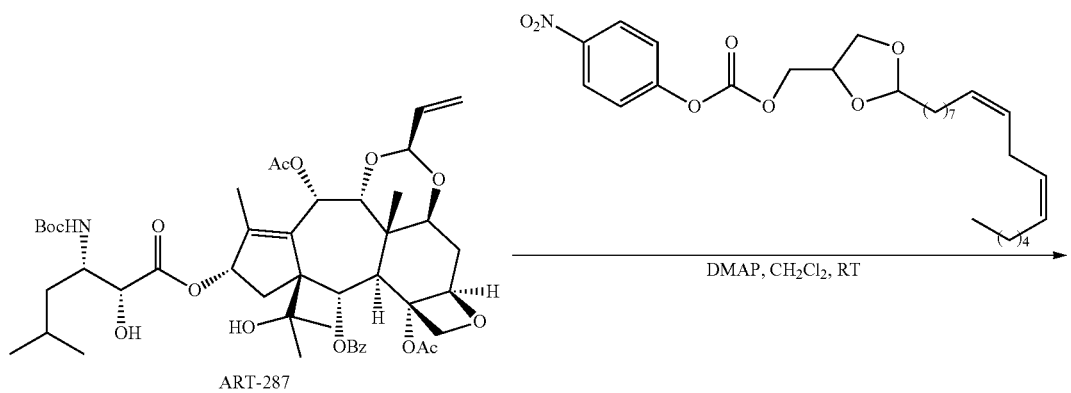

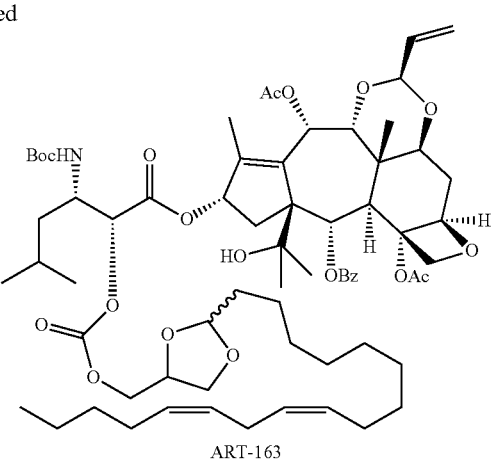

ART-163

ART 209 was prepared by following the procedure as outlined in Method A. HPLC retention time 9.6, Method: Taxane conjugates_MKG18 (Synergy column, ACN/H$_2$O 80/20 10 min, 100% ACN 2 min, 230 nm, 1.5 ml/min, 30° C., 15 min). +TOF MS: m/z 1253.7505 [M+18] (M+NH$_4^+$)

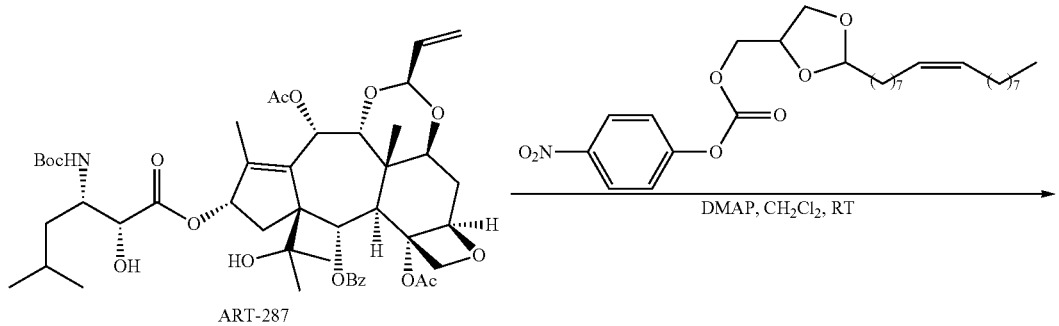

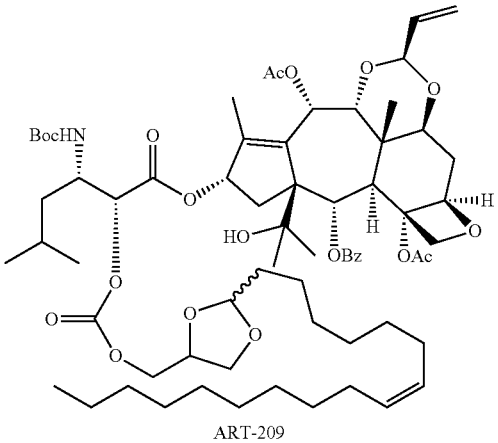

ART-209

Cytotoxicity of Specific Compounds:
MTS Proliferation Assay using SK-N-AS Cells

Day 1: SK-N-AS cells were plated in appropriate growth medium at 5×10$^3$ per well in 100 µL in 96 well tissue culture plates, Falcon, one plate for each drug to be tested. Column 1 was blank; it contained medium, but no cells. The plates were incubated overnight at 37° C. in 5% CO$_2$ to allow attachment.

Day 2: Drug diluted in culture media was added to the cells at a concentration of 0.005 nM to 10 µM, in quadruplicate. After 48-72 hours of drug exposure, the MTS agent was added to all wells and incubated 1-6 hrs (37° C., 5% CO$_2$), depending on cell type, as per CellTiter 96® AQueous Non-Radioactive Cell Proliferation Assay (MTS), Promega. Plates were processed using a Bio-Tek Synergy HT Multi-detection microtiter plate reader at 490 nanometer wavelength and data were processed with KC4V.3 software. Data plots of drug concentration vs. absorbance were plotted and the concentration resulting in 50% inhibition (IC$_{50}$) was extrapolated for each of the tested compounds.

As summarized in Table 1, the IC$_{50}$ value for each tested compound in the SK-N-AS cell line was determined. The clinical comparator drug, paclitaxel, was included in the experiment to allow comparison of the results of the candidate compounds to a clinically relevant standard in the taxane class.

TABLE 1

IC$_{50}$ (nM) Values in SK-N-AS
IC$_{50}$ (nM) Values in SK-N-AS
(MDR− Neuroblastoma)

| Compound | IC$_{50}$ |
|---|---|
| ART 449 | 4.0 ± 0.5 |
| ART 448 | 5.0 ± 0.7 |
| ART 473 | 12.6 ± 0.9 |
| ART 471 | 261.6 ± 12 |
| ART 470 | 349.1 ± 15 |
| ART 488 | 0.33 ± 0.1 |
| ART 441 | 1.76 ± 0.5 |
| ART 472 | 1.19 ± 0.5 |
| ART 332 | 1.1 ± 0.5 |
| ART 273 | 2.0 ± 0.5 |
| ART 467 | 273.9 ± 12 |
| Paclitaxel | 0.05 ± 0.01 |

MTT Proliferation Assay Using Paired MDR+ and MDR− Cell Lines

A second evaluation of the cytotoxicity of the acid labile, lipophilic molecular conjugates was undertaken. The purpose of these experiments was to compare the toxicity of the conjugates in multidrug resistant cells and their parental susceptible lines to test the hypothesis that a subset of these compounds would exhibit a similar level of toxicity in the drug resistant lines as that observed in the parent susceptible cell line.

MTT-based cytotoxicity assays were performed using human cancer cell lines and paired sublines exhibiting multidrug resistance. These lines included a uterine sarcoma line, MES-SA, and its doxorubicin-resistant subline, MES-SA/Dx5. See W. G. Harker, F. R. MacKintosh, and B. I. Sikic. Development and characterization of a human sarcoma cell line, MES-SA, sensitive to multiple drugs. *Cancer Research* 43: 4943-4950 (1983); W. G. Harker and B. I. Sikic. Multidrug (pleiotropic) resistance in doxorubicin-selected variants of the human sarcoma cell line MES-SA. *Cancer Research* 45: 4091 4096 (1985).

MES-SA/Dx5 exhibits a marked cross resistance to a number of chemotherapeutic agents including vinblastine, paclitaxel, colchicine, vincristine, etoposide, dactinomycin, mitoxantrone and daunorubicin and moderate cross resistance to mitomycin C and melphalan. However, resistance to bleomycin, cisplatin, carmustine, 5-fluorouracil or methotrexate is not observed. MES-SA/Dx5 cells express high levels of ABCB1 (MDR1) mRNA and its gene product, the P-glycoprotein. MES-SA and MES-SA/Dx5 were purchased from the American Type Culture Collection (ATCC, Manassas, Va.).

The second set of cells tested, CCRF-CEM or simply CEM, were derived from the blood of a patient with acute lymphoblastic leukemia. G. E. Foley, H. Lazarus, S. Farber, B. G. Uzman, B. A. Boone, and R. E. McCarthy. Continuous culture of human lymphoblasts from peripheral blood of a child with acute leukemia. *Cancer* 18: 522-529 (1965). The subline CEM/VLB$_{100}$ was developed to be resistant to up to vinblastine at 100 ng/ml. W. T. Beck, T. J. Mueller, and L. R. Tanzer. Altered surface membrane glycoproteins in Vinca alkaloid-resistant human leukemic lymphoblasts. *Cancer Research* 39: 2070-2076 (1979). Drug resistance is achieved by overexpression of the MDR1 gene. Resistance in the CEM subline designated CEM/VM-1-5, however, is "atypical." M. K. Danks, J. C. Yalowich, and W. T. Beck. Atypical multiple drug resistance in a human leukemic cell line selected for resistance to teniposide (VM-26). *Cancer Research* 47: 1297-1301 (1987). The classes of drugs included in the "classic" multiple drug resistance phenotype are Vinca alkaloids, anthracyclines, epipodophyllotoxins and antibiotics. However, CEM/VM-1-5 cells retain sensitivity to the Vinca alkaloids despite resistance and cross-resistance to etoposide, anthracyclines and mitoxantrone. Danks, M. K.; Schmidt, C. A.; Cirtain, M. C.; Suttle, D. P.; Beck, W. T., Altered catalytic activity of and DNA cleavage by DNA topoisomerase II from human leukemic cells selected for resistance to VM-26. *Biochemistry* 1988, 27, 8861-8869. Resistance in CEM/VM-1-5 cells is effected by over expression of the ABCC1 (MRP1) gene. CEM, CEM/VLB$_{100}$ and CEM/VM-1-5 cells were obtained from Dr. W T Beck, University of Illinois at Chicago.

TABLE 2

Summary of Testing Concentrations in Paired Cell Lines
Summary of Testing Concentrations

| Compound | Test Concentrations (ng/ml) |
|---|---|
| ART 273 | 200, 40, 8, 1.6, 0.32, 0.064 |
| ART 198 | 5,000, 1,000, 200, 40, 8, 1.6 |
| ART 488 | 5,000, 1,000, 200, 40, 8, 1.6 |
| ART 489 | 5,000, 1,000, 200, 40, 8, 1.6 |
| Paclitaxel | 25,000 5,000, 1,000, 200, 40, 8, 1.6 |
| Vinblastine | |
| Doxorubicin | |

TABLE 3

IC50 Results (nM)

| Compound | MES-SA (Hs) | MES-SA/Dx5 (MDR + Hs) | Degree of resistance[1] | CEM (HTL) | GEM/VLB$_{100}$ (MDR + HTL) | Degree of resistance[2] | CEM/VM-1-5 (MDR + HTL) | Degree of resistance[2] |
|---|---|---|---|---|---|---|---|---|
| ART 273 Q1 | 1.5 ± 0.7 | 7 ± 4 | 4.5 ± 0.7 | 2 ± 0 | 36 ± 20 | 18 ± 10 | 7 ± 2 | 3 ± 1 |
| ART 488 Q1 prodrug | 1.5 ± 0.7 | 7 ± 5.7 | 4.3 ± 1.8 | 4 ± 0 | 34 ± 12 | 9 ± 4 | 8 ± 4 | 2 ± 1 |
| ART 198 Q2 | 47.5 ± 11 | 376 ± 110 | 7.9 ± 0.6 | 113 ± 53 | 7186 ± 1918 | 76 ± 52 | 308 ± 10 | 3 ± 1 |
| ART 489 Q2 prodrug | 5.5 ± 3.5 | 17 ± 5.7 | 4.3 ± 3.8 | 21 ± 2 | 670 ± 71 | 33 ± 0 | 24 ± 4 | 1.2 ± 0.07 |

TABLE 3-continued

| | IC50 Results (nM) | | | | | | | |
|---|---|---|---|---|---|---|---|---|
| Compound | MES-SA (Hs) | MES-SA/Dx5 (MDR + Hs) | Degree of resistance[1] | CEM (HTL) | GEM/VLB$_{100}$ (MDR + HTL) | Degree of resistance[2] | CEM/VM-1-5 (MDR + HTL) | Degree of resistance[2] |
| Paclitaxel | 9 ± 7 | 19398 ± 204 | 3105 ± 2416 | <11/2 | 3029/1295 | >275/648 | <11/8 | 4 |
| Vinblastine | 1.1 ± 0.3 | 43 ± 12 | 38.5 ± 0.7 | 1 ± 0.8 | 227 ± 77 | 255 ± 127 | 1.3 ± 0.9 | 1.2 ± 0.07 |
| Doxorubicin | 2 | 97 | 49 | 14 | 2100 | 150 | 3060 | 219 |

Data are expressed as IC$_{50}$ values (nM).
[1]Calculated by dividing the IC$_{50}$ of the resistant lines by the IC$_{50}$ of the sensitive MES-SA cells.
[2]Calculated by dividing the IC$_{50}$ of the resistant lines by the IC$_{50}$ of the sensitive CEM cells.
HTL means Human T-Lymphoblastoid; Hs means Human sarcoma.

The observed cytotoxicity of the acid labile, lipophilic molecular conjugates demonstrates that they still possess the anti-cancer activity desired for them to retain utility as potential chemotherapeutic agents. It is especially noteworthy that the apparent degree of resistance expressed by the resistant cell lines is diminished by 20 to 50% for the acid labile, lipophilic molecular conjugates. This was an unexpected result.

Stability of Acid Labile, Lipophilic Molecular Conjugates in Plasma:

The stability of the acid labile, lipophilic molecular conjugates to hydrolysis in plasma was evaluated to determine their potential to release the active cancer chemotherapeutic agents into systemic circulation and thereby cause general off target toxicity ("side effects"). The conjugates were incubated with plasma of mouse, rat and human origin.

HPLC grade Methanol from Fisher (Fair lawn, N.J., USA). Part No: A452-4 (074833). HPLC grade Water from Fisher (Fair lawn, N.J., USA). Part No: W5-4 (073352). Drug-free mouse, rat and human plasmas were purchased from Innovative Research Inc. (Southfield, Mich., USA). Liposyn® I.V. Fat Emulsion from Hospira, Inc. (Lake Forest, Ill.).

Preparation of Plasma Incubations:

Each drug (ART 198, ART 273, ART 488 and ART 489) was prepared in triplicate in mouse, rat and human plasma individually at 10 µg/ml concentration and vortexed for 1 minute and placed in a water bath at 37° C. at a shake rate of 75 per minute. Samples were drawn at time points of 0, 15, 30, 45, 60, 75, 90, 105, 120, 135, 150, 165, 180, 210, 240, 300, 360 and 480 minutes.

Analytical Method for ART 198, ART 273, ART 488 and ART 489 Analysis in Plasma:

Chromatographic separation of the compounds was performed on a Waters Acquity UPLC™ using a BEH C$_{18}$ column (1.7 µm, 2.1×50 mm). The mobile phase consisted of Methanol: 0.1% Formic acid (80:20). The flow rate was 0.3 ml/min; the sample injection volume was 5 µL, resulting in a 3 minute run time.

The MS instrumentation consisted of a Waters Micromass Quattro Micro™ triple-quadrapole system (Manchester, UK). The MS system was controlled by a 4.0 version of MassLynx software. Ionization was performed in the positive electrospray ionization mode. MS/MS conditions were the following: capillary voltage 3.02 kV; cone voltage 50 v; extractor voltage 5 v; and RF lens voltage 0.5 v. The source and desolvation temperatures were 100° C. and 400° C. respectively, and the desolvation and cone gas flow were 400 and 30 L/hr, respectively.

The selected mass-to-charge (m/z) ratio transitions of the ART 198 used in the selected ion monitoring (SIM) were: for ART 198, 617 (M+K)$^+$, for ART 273, 589 (M+K)$^+$, for ART 488, 913 (M+Na)$^+$, and for ART 489, 957 (M+Na)$^+$. The dwell time was set at 200 msec. MS conditions were optimized using direct infusion of standard solutions prepared in methanol and delivered by a syringe pump at a flow rate of 20 µL/min.

Plasma Sample Preparation:

Samples of 100 µL were collected at time points of 0, 15, 30, 45, 60, 75, 90, 105, 120, 135, 150, 165, 180, 210, 240, 300, 360 and 480 minutes respectively and the reaction was terminated with methanol. In a separate set of experiments the acid labile, lipophilic molecular conjugates were dissolved in a small amount of ethanol and diluted into a lipid emulsion (Liposyn®) and added to mouse and human plasma before incubation and the hydrolysis of the conjugates was similarly measured. Collected plasma samples of 100 µL, containing drug were placed in separate Eppendorf micro centrifuge tubes for processing. Methanol (200 µL) was added to extract the drug using the protein precipitation technique. The micro tubes were then vortex mixed for 10 minutes and centrifuged for 15 minutes at a speed of 10,000 rpm (Eppendorf 5415C centrifuge). The supernatant was collected and filtered using a 0.45 µm filter (Waters 13 mm GHP 0.45 µm) before analysis.

UPLC/MS/MS analysis of blank mouse, rat and human plasma samples showed no endogenous peak interference with the quantification of ART 198, ART 273, ART 488 or ART 489.

The weighted linear least-squares (1/x) regression was used as the mathematical model. The coefficient (r) for the compounds ranged from 0.9925 to 0.9999. The calibration range was selected according to the concentrations anticipated in the samples to be determined. The final calibration range was 10-12,500 ng/mL with a lower limit of quantification of 10 ng/mL.

The repeatability and reproducibility bias (%) is within the acceptance limits of ±20% at low concentration and ±15% at other concentration levels with RSD's of less than 5% at all concentrations evaluated.

The mean recoveries of the method were in the range of 86.22-99.83% at three different concentrations of the test drugs from plasma. These results suggested that there was no relevant difference in extraction recovery at different concentration levels.

Incubations of ART 467 and Paclitaxel:

A 0.2 ml aliquot from 210.6 µg/ml stock solution of ART 467 was spiked into 3.8 ml of human plasma preincubated for 15 min (37° C.) and incubated in a reciprocating water bath at 37° C. Samples were drawn at 0, 0.5, 1, 2, 3, 4, 6, 8, 10, 12 and 24 hours.

Analytical Method for ART 467 and Paclitaxel (Liquid Chromatography-Tandem Mass Spectrometry):

Chromatographic separation was carried out using an ACQUITY UPLC liquid chromatograph (Waters Corporation, Milford, Mass., USA) consisting of a binary pump, autosampler, degasser and column oven. A mobile phase of methanol-acetonitrile (50:50, v/v) was pumped at a flow-rate of 0.4 ml/min through an ACQUITY UPLC BEH $C_{18}$ column (1.7 μm, 2.1×50 mm i.d., Waters Corporation) maintained at 25° C. 10 μl of sample was injected and the run time was 3.0 min. The LC elute was connected directly to an ESCi triple-quadrapole mass spectrometer equipped with an electrospray ionization (ESI) ion source. The quadrapoles were operated in the positive ion mode. The multiple reaction monitoring (MRM) mode was used for quantification using MassLynx version 4.1 software. Mass transitions of m/z 876.2, 307.9; 882.2, 313.9; and 1216.5, 647.8 were optimized for paclitaxel Na+ adduct, $^{13}C6$-paclitaxel adduct and ART 467 adduct respectively, with dwell time of 0.5 s. Nitrogen was used as nebulizing gas (30 l/h) and desolvation gas (300 l/h) with a desolvation temperature at 250° C., and argon was collision gas. The capillary voltage was set at 3.5 kV, and cone voltage at 90 V. The source temperature was set at 100° C.

Plasma Sample Preparation:

At the different time periods (0, 0.5, 1, 2, 3, 4, 6, 8, 10, 12 and 24 h), 200 μl aliquot of samples were taken and immediately added to 1.3 ml of cold TBME and subsequently 20 μl of internal standard stock solution (80.7 μg/ml in methanol) was added. Each tube was vortex mixed for approximately 2 min and then centrifuged at 13000 rpm for 10 min 1.0 ml of resultant supernatant was transferred to another tube and dried under a stream of nitrogen gas at 35° C. Each dried residue was reconstituted with 200 μl of methanol and vortex mixed for 0.5 min. After centrifugation at 13000 rpm for 10 min, the supernatants were transferred to HPLC autosampler vials, and 10 μl aliquot of each sample was injected into LC-MS-MS.

Samples were collected at various times and the per cent remaining of the acid labile, lipophilic molecular conjugate of the cancer chemotherapeutic agent was determined along with the per cent of the chemotherapeutic agent released from the hydrolysis of the conjugate. The results are presented in table format and graphically.

Stability of Unconjugated ART 273 in Plasma:

The intrinsic stability of unconjugated ART 273 in mouse, rat and human plasma was determined. Without reference to any particular kinetic model it is seen that approximately 30%, 54%, and 67% of the initial ART 273 remains after 480 minutes in mouse, rat and human plasma, respectively.

Stability of the ART 273 Conjugate, ART 488, in Plasma

The intrinsic stability of the ART 273 Conjugate, ART 488, in mouse, rat and human plasma was determined. Without reference to any particular kinetic model it is seen that approximately 36%, 33%, and 44% of the initial ART 488 remains after 480 minutes in mouse, rat and human plasma, respectively. Also without reference to any particular kinetic model it is seen that the formation of ART 273 approximately equivalent to 36%, 32%, and 37% of the initial ART 488 is present after 480 minutes in mouse, rat and human plasma, respectively.

Stability of the ART 273 Conjugate, ART 488, in Plasma when Added in a Lipid Emulsion:

The intrinsic stability of the ART 273 Conjugate, ART 488, in mouse and human plasma was determined. Without reference to any particular kinetic model it is seen that approximately 89% and 88% of the initial ART 488 remains after 480 minutes in mouse and human plasma, respectively.

Stability of Unconjugated ART 198 in Plasma:

The intrinsic stability of unconjugated ART 198 in mouse, rat and human plasma was determined. Without reference to any particular kinetic model it is seen that approximately 26%, 30%, and 34% of the initial ART 198 remains after 480 minutes in mouse, rat and human plasma, respectively.

Stability of the ART 198 Conjugate, ART 489, in Plasma:

The intrinsic stability of the ART 198 Conjugate, ART 489, in mouse, rat and human plasma was determined. Without reference to any particular kinetic model it is seen that approximately 34%, 34%, and 66% of the initial ART 489 remains after 480 minutes in mouse, rat and human plasma, respectively. Also without reference to any particular kinetic model it is seen that ART 198 equivalent to approximately 35%, 32%, and 20% of the initial ART 489 is present after 480 minutes in mouse, rat and human plasma, respectively.

Stability of the ART 198 Conjugate, ART 489, in Plasma when Added in a Lipid Emulsion:

The intrinsic stability of the ART 198 Conjugate, ART 489, in mouse and human plasma was determined. Without reference to any particular kinetic model it is seen that approximately 73% and 77% of the initial ART 489 remains after 480 minutes in mouse and human plasma, respectively.

Stability of the Paclitaxel Conjugate, ART 467, in Plasma:

The intrinsic stability of the paclitaxel conjugate, ART 467, in human plasma was determined Without reference to any particular kinetic model it is seen that approximately 41% of the initial ART 467 remains after 1440 minutes in human plasma. Also without reference to any particular kinetic model it is seen that paclitaxel equivalent to approximately 16% of the initial ART 467 is present after 1440 minutes in human plasma.

Dissolution of the acid labile, lipophilic molecular conjugates ART 488 and ART 489 in a lipid emulsion before addition to plasma enhanced the stability of the conjugate to hydrolysis by the plasma medium dramatically (summarized in Table 11). That the acid labile, lipophilic molecular conjugates remained within the lipid emulsion and did not "leak" into the plasma phase of the incubation is evident from the lack of release of the free drug from the conjugates. No detectable concentrations of free drug could be observed in the incubations wherein the conjugates were first dissolved in the lipid emulsion before addition to the incubation medium (see Table 6 and Table 9).

Estimation of Maximum Tolerated Dose (MTD) of Acid Labile, Lipophilic Molecular Conjugates in the Mouse:

Stock solutions of ART 198 and 273 and their respective acid labile, lipophilic molecular conjugates (ART 489 and ART 488, respectively) were prepared in ethanol and then diluted into a lipid emulsion (Intralipid) and injected intravenously into mice at various doses in milligrams per kilogram. The animals were observed daily for signs of toxicity and/or death for a period of 30 days. The MTD was defined as survival of the dosed mice for the full 30 day observation period.

The MTD of ART 198 was determined to be 4.0+/−1.0 mg/kg; the MTD of ART 273 was determined to be 1.0+/−0.5 mg/kg; the MTD of ART 489 was determined to be 3.1+/−1.0 mg/kg; and the MTD of ART 488 was determined to be 4.0+/−0.5 mg/kg.

The observed similarity of MTD for ART 198 and its acid labile, lipophilic molecular conjugate ART 489, or in the case of ART 273, the increase from an MTD of roughly 1 mg/kg for ART 273 to roughly 4 mg/kg for its acid labile, lipophilic molecular conjugate ART 488 is surprising in light of their observed in vitro cytotoxicities. In in vitro cytotoxicity evaluations, the acid labile, lipophilic molecular conjugates of ART 273 are routinely observed to be nearly an order of magnitude (10×) more potent than ART 273. The MTD determination results suggest that the acid labile, lipophilic molecular conjugates of cancer chemotherapeutic agent may be more useful for treating patients due to reduced toxicity.

TABLE 4

Stability of ART 273 in Plasma at 37° C.

| Time, min | ART 273 in Mouse Plasma ART 273 | ART 273 in Rat Plasma ART 273 | ART 273 in Human Plasma ART 273 |
|---|---|---|---|
| 0 | 100 | 100 | 100 |
| 15 | 81.1 | 87.9 | 97.2 |
| 30 | 76.0 | 84.9 | 96.5 |
| 45 | 68.4 | 82.9 | 94.6 |
| 60 | 65.4 | 78.9 | 93.5 |
| 75 | 62.7 | 71.8 | 93.5 |
| 90 | 54.8 | 69.7 | 92.2 |
| 105 | 53.8 | 66.1 | 89.4 |
| 120 | 49.8 | 64.6 | 87.0 |
| 135 | 46.8 | 64.3 | 86.6 |
| 150 | 44.0 | 61.8 | 85.5 |
| 165 | 42.2 | 57.0 | 83.8 |
| 180 | 39.5 | 56.7 | 83.4 |
| 210 | 37.6 | 55.4 | 80.4 |
| 240 | 36.4 | 55.1 | 80.0 |
| 300 | 33.8 | 54.7 | 73.2 |
| 360 | 31.5 | 54.5 | 69.3 |
| 480 | 30.1 | 53.9 | 66.7 |

TABLE 5

Stability of ART 488 in Plasma at 37° C.

| | ART 488 in Mouse Plasma | | ART 488 in Mouse Plasma | | ART 488 in Human Plasma | |
|---|---|---|---|---|---|---|
| Time, min | ART 488 | ART 273 | ART 488 | ART 273 | ART 488 | ART 273 |
| 0 | 100 | 0 | 100 | 0 | 100 | 0 |
| 15 | 91.2 | 3.3 | 90.7 | 2.2 | 90.8 | 1.2 |
| 30 | 85.7 | 7.9 | 80.6 | 8.7 | 89.1 | 7.3 |
| 45 | 81.3 | 10.7 | 79.8 | 10.1 | 87.8 | 9.3 |
| 60 | 75.0 | 11.3 | 78.3 | 11.7 | 87.9 | 10.3 |
| 75 | 73.2 | 12.2 | 78.0 | 12.4 | 87.9 | 11.2 |
| 90 | 65.2 | 13.2 | 77.5 | 13.2 | 87.1 | 12.5 |
| 105 | 58.8 | 14.4 | 73.7 | 14.0 | 86.2 | 13.4 |
| 120 | 56.4 | 16.3 | 69.5 | 16.3 | 85.3 | 15.1 |
| 135 | 56.2 | 18.2 | 69.1 | 19.5 | 84.0 | 19.7 |
| 150 | 55.0 | 19.2 | 68.7 | 20.0 | 82.7 | 19.9 |
| 165 | 53.7 | 22.5 | 64.0 | 22.1 | 81.1 | 23.3 |
| 180 | 53.7 | 26.1 | 63.8 | 24.7 | 78.6 | 26.5 |
| 210 | 52.4 | 27.9 | 63.6 | 25.5 | 78.1 | 28.1 |
| 240 | 50.3 | 28.7 | 60.4 | 26.7 | 76.5 | 29.3 |
| 300 | 48.2 | 29.3 | 53.7 | 28.0 | 59.3 | 30.8 |
| 360 | 45.6 | 30.1 | 48.7 | 29.0 | 59.8 | 32.2 |
| 480 | 35.7 | 35.6 | 33.3 | 32.2 | 43.6 | 36.6 |

TABLE 6

Stability of ART 488 in Plasma at 37° C. When Added in a Lipid Emulsion

| | ART 488 in Liposyn ® in Mouse Plasma | | ART 488 in Liposyn ® in Human Plasma | |
|---|---|---|---|---|
| Time, min | ART 488 | ART 273 | ART 488 | ART 273 |
| 0 | 100 | ND | 100 | ND[a] |
| 15 | 98.7 | ND | 98.3 | ND |
| 30 | 98.2 | ND | 97.3 | ND |
| 45 | 97.4 | ND | 96.1 | ND |
| 60 | 96.9 | ND | 95.8 | ND |
| 75 | 97.0 | ND | 95.3 | ND |
| 90 | 98.3 | ND | 95.6 | ND |
| 105 | 96.0 | ND | 94.6 | ND |
| 120 | 95.2 | ND | 94.5 | ND |
| 135 | 93.8 | ND | 92.5 | ND |
| 150 | 93.1 | ND | 92.2 | ND |
| 165 | 92.9 | ND | 91.9 | ND |
| 180 | 91.8 | ND | 91.0 | ND |
| 210 | 91.7 | ND | 91.0 | ND |
| 240 | 91.4 | ND | 90.7 | ND |
| 300 | 91.3 | ND | 90.7 | ND |
| 360 | 90.0 | ND | 90.2 | ND |
| 480 | 88.5 | ND | 88.1 | ND |

[a]ND = None detected

TABLE 7

Stability of ART 198 in Plasma at 37° C.

| Time, min | ART 198 in Mouse Plasma ART 198 | ART 198 in Rat Plasma ART 198 | ART 198 in Human Plasma ART 198 |
|---|---|---|---|
| 0 | 100 | 100 | 100 |
| 15 | 96.8 | 95.8 | 99.3 |
| 30 | 94.0 | 84.0 | 99.1 |
| 45 | 85.5 | 66.0 | 94.9 |
| 60 | 82.0 | 55.7 | 94.6 |
| 75 | 72.6 | 54.4 | 93.1 |
| 90 | 66.9 | 54.2 | 89.9 |
| 105 | 63.2 | 54.0 | 87.0 |
| 120 | 59.2 | 52.1 | 68.5 |
| 135 | 57.4 | 48.9 | 66.4 |
| 150 | 51.9 | 48.9 | 61.1 |
| 165 | 46.2 | 45.4 | 59.6 |
| 180 | 43.0 | 44.0 | 48.6 |
| 210 | 39.3 | 42.7 | 47.6 |
| 240 | 35.4 | 42.2 | 46.0 |

TABLE 7-continued

Stability of ART 198 in Plasma at 37° C.

| Time, min | ART 198 in Mouse Plasma ART 198 | ART 198 in Rat Plasma ART 198 | ART 198 in Human Plasma ART 198 |
|---|---|---|---|
| 300 | 32.4 | 34.3 | 44.4 |
| 360 | 28.8 | 30.1 | 39.6 |
| 480 | 25.9 | 30.1 | 34.2 |

TABLE 8

Stability of ART 489 in Plasma at 37° C.

| | ART 489 in Mouse Plasma | | ART 489 in Rat Plasma | | ART 489 in Human Plasma | |
|---|---|---|---|---|---|---|
| Time, min | ART 489 | ART 198 | ART 489 | ART 198 | ART 489 | ART 198 |
| 0 | 100 | 0 | 100 | 0 | 100 | 0 |
| 15 | 95.7 | 1.7 | 93.2 | 3.1 | 99.3 | 0.1 |
| 30 | 88.6 | 6.1 | 75.8 | 14.1 | 98.8 | 0.6 |
| 45 | 84.8 | 10.0 | 74.3 | 16.3 | 98.4 | 0.9 |
| 60 | 79.2 | 14.6 | 75.0 | 18.1 | 97.4 | 1.1 |
| 75 | 78.1 | 16.7 | 74.4 | 20.5 | 94.6 | 1.2 |
| 90 | 70.1 | 18.2 | 74.4 | 20.8 | 93.7 | 2.4 |
| 105 | 68.0 | 20.3 | 73.7 | 21.4 | 93.0 | 3.2 |
| 120 | 64.1 | 21.3 | 69.9 | 21.9 | 91.9 | 5.1 |
| 135 | 63.2 | 22.1 | 68.5 | 22.3 | 91.7 | 6.5 |
| 150 | 59.4 | 25.1 | 67.3 | 22.9 | 90.9 | 7.2 |
| 165 | 54.7 | 26.4 | 63.0 | 23.6 | 90.4 | 8.5 |
| 180 | 51.6 | 27.6 | 63.0 | 24.5 | 90.1 | 9.6 |
| 210 | 50.3 | 29.7 | 62.7 | 25.0 | 89.0 | 12.3 |
| 240 | 47.5 | 32.0 | 61.7 | 25.3 | 86.7 | 14.2 |
| 300 | 41.1 | 34.1 | 55.4 | 26.1 | 84.1 | 16.3 |
| 360 | 38.1 | 34.3 | 48.2 | 28.0 | 78.7 | 19.5 |
| 480 | 34.0 | 34.7 | 34.3 | 32.3 | 65.9 | 20.4 |

TABLE 9

Stability of ART 489 in Plasma at 37° C. When Added in a Lipid Emulsion

| | ART 489 in Liposyn ® in Mouse Plasma | | ART 489 in Liposyn ® in Human Plasma | |
|---|---|---|---|---|
| Time, min | ART 489 | ART 198 | ART 489 | ART 198 |
| 0 | 100 | ND | 100 | ND |
| 15 | 98.0 | ND | 98.4 | ND |
| 30 | 97.9 | ND | 93.9 | ND |
| 45 | 97.4 | ND | 92.7 | ND |
| 60 | 91.4 | ND | 88.2 | ND |
| 75 | 90.3 | ND | 87.9 | ND |
| 90 | 87.9 | ND | 87.5 | ND |
| 105 | 80.7 | ND | 86.4 | ND |
| 120 | 80.4 | ND | 86.4 | ND |
| 135 | 79.9 | ND | 84.7 | ND |
| 150 | 79.2 | ND | 84.6 | ND |
| 165 | 78.7 | ND | 83.7 | ND |
| 180 | 78.2 | ND | 82.9 | ND |
| 210 | 75.6 | ND | 82.0 | ND |
| 240 | 74.7 | ND | 81.4 | ND |
| 300 | 73.7 | ND | 80.2 | ND |
| 360 | 73.0 | ND | 78.2 | ND |
| 480 | 72.9 | ND | 76.6 | ND |

TABLE 10

Stability of ART 467 in Human Plasma at 37° C.

| | ART 467 in Human Plasma | |
|---|---|---|
| Time, min | ART 467 | Paclitaxel |
| 0 | 100.0 | 0.0 |
| 30 | 86.3 | 0.7 |
| 60 | 78.0 | 1.7 |
| 120 | 76.0 | 2.7 |
| 180 | 75.0 | 3.8 |
| 240 | 73.7 | 5.5 |
| 360 | 72.8 | 8.2 |
| 480 | 70.5 | 10.3 |
| 600 | 68.2 | 12.4 |
| 720 | 64.6 | 14.1 |
| 1440 | 41.3 | 15.5 |

TABLE 11

Drug Stabilization by Incorporation in a Lipid Emulsion
% of Initial Drug Remaining After 480 Minutes

| | Mouse Plasma | Rat Plasma | Human Plasma |
|---|---|---|---|
| ART 273 | 30.1 | 53.9 | 66.7 |
| ART 488 | 35.7 | 33.3 | 43.6 |
| ART 488 in Liposyn | 88.5 | NP | 88.1 |
| ART 198 | 25.9 | 30.1 | 34.2 |
| ART 489 | 34.0 | 34.3 | 65.9 |
| ART 489 in Liposyn | 72.9 | NP [a] | 76.6 |

[a] NP = Experiment not performed

What is claimed is:

1. An acid labile lipophilic molecular conjugate (ALLMC) of the formula 1, 1.1 or formula 2:

[Structure 1]

[Structure 1.1]

[Structure 2]

wherein:
R is a hydroxyl bearing cancer chemotherapeutic agent;
for formula 1 or 1.1:
$R^1$ is hydrogen, $C_1$-$C_4$ alkyl or $C_5$-$C_{22}$ alkyl;
$R^2$ is $C_5$-$C_{22}$ alkyl;
Y is selected from O, NR' or S wherein R' is hydrogen or $C_1$-$C_6$ alkyl;
Z is O or S;
Q is O or S; and T is O or S;
for formula 2:
$R^2$ is a $C_1$-$C_{22}$ alkyl;
T is O or S; and
X is a hydrogen or a leaving group selected from the group consisting of mesylates, sulfonates and halogen (Cl, Br and I);
and their isolated enantiomers, diastereoisomers or mixtures thereof;
or a pharmaceutically acceptable salt thereof.

2. The acid labile lipophilic molecular conjugate of claim 1 of the formula 1 or 1.1:
wherein:
R is a hydroxyl bearing cancer chemotherapeutic agent;
$R^1$ is hydrogen, $C_1$-$C_4$ alkyl or $C_5$-$C_{22}$ alkyl;
$R^2$ is $C_5$-$C_{22}$ alkyl;
Y is O or S;
Z is O; and
Q is O; and T is O.

3. The acid labile lipophilic molecular conjugate of claim 1 of the formula 2:
wherein:
$R^2$ is $C_5$-$C_{22}$ alkyl;
T is O; and
X is hydrogen or is selected from the group consisting of Cl, Br and I.

4. The acid labile lipophilic molecular conjugate of claim 1 comprising the formula 1a, 1b or formula 2a:

[Structure 1a]

[Structure 1b]

[Structure 2a]

wherein:
R is a hydroxyl bearing cancer chemotherapeutic agent (HBCCA);
for formula 1a or 1b:
$R^1$ is hydrogen, $C_1$-$C_4$ alkyl or $C_5$-$C_{22}$ alkyl; and
$R^2$ is $C_5$-$C_{22}$ alkyl;
for formula 2a:
$R^2$ is $C_1$-$C_{22}$ alkyl; and
X is hydrogen or is selected from the group consisting of Cl, Br and I.

5. The acid labile lipophilic molecular conjugate of claim 1, wherein the hydroxyl bearing cancer chemotherapeutic agent is selected from the group consisting of taxanes, abeotaxanes, camptothecins, epothilones, cucurbitacins, quassinoids, anthracyclines, and their analogs and derivatives.

6. The acid labile lipophilic molecular conjugate of claim 1, wherein the hydroxyl bearing cancer chemotherapeutic agent is selected from the group consisting of aclarubicin, camptothecin, masoprocol, paclitaxel, pentostatin, amrubicin, cladribine, cytarabine, docetaxel, elliptinium acetate, epirubicin, etoposide, formestane, fulvestrant, gemcitabine, idarubicin, pirarubicin, topotecan, valrubicin and vinblastine.

Figure 20:
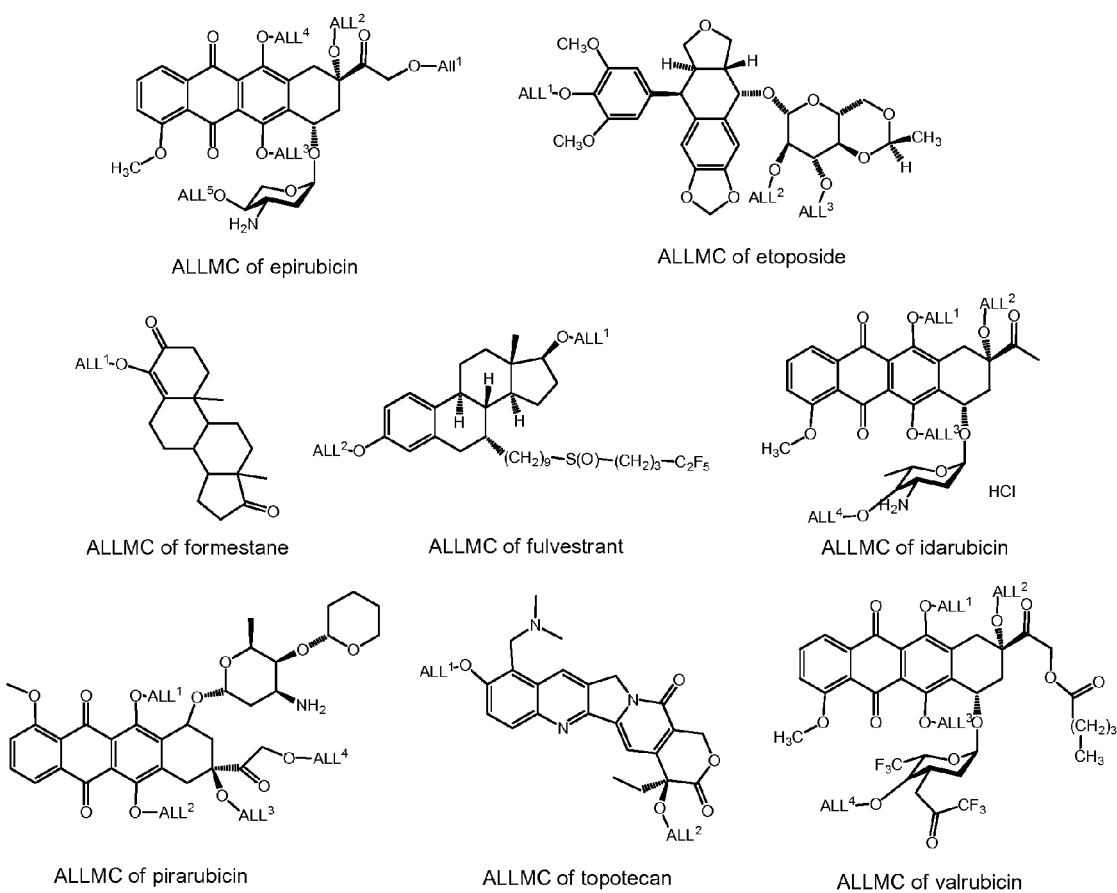

7. The acid labile lipophilic molecular conjugate of claim 1, wherein the conjugate is selected from the compounds in FIG. 18, FIG. 19 and FIG. 20.

8. A pharmaceutical composition comprising: a) a therapeutically effective amount of a compound of claim 1, in the form of a single diastereoisomer; and b) a pharmaceutically acceptable excipient.

9. A method for the treatment of cancer in a patient comprising administering to the patient a therapeutically effective amount of a compound or composition of claim 1, to a patient in need of such treatment.

10. The method of claim 9, wherein the cancer is selected from the group consisting of leukemia, neuroblastoma, glioblastoma, cervical, colorectal, pancreatic, renal and melanoma.

11. The method of claim 9, wherein the cancer is selected from the group consisting of lung, breast, prostate, ovarian and head and neck.

12. The method of claim 9, wherein the method provides at least a 10% to 50% diminished degree of resistant expressed by the cancer cells when compared with the non-conjugated hydroxyl bearing cancer chemotherapeutic agent.

13. A method for reducing or substantially eliminating the side effects of chemotherapy associated with the administration of a cancer chemotherapeutic agent to a patient, the method comprising administering to the patient a therapeutically effective amount of an acid labile lipophilic molecular conjugate of the formula 1, 1.1 or formula 2:

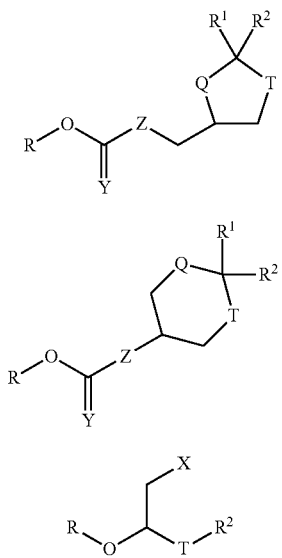

wherein:
R is a hydroxyl bearing cancer chemotherapeutic agent;
for formula 1 or 1.1:
$R^1$ is hydrogen, $C_1$-$C_4$ alkyl or $C_5$-$C_{22}$ alkyl;
$R^2$ is $C_5$-$C_{22}$ alkyl;
Y is selected from O, NR' or S wherein R' is hydrogen or $C_1$-$C_6$ alkyl;
Z is O or S; and
Q is O or S; and T is O or S;
for formula 2:
$R^2$ is $C_1$-$C_{22}$ alkyl;
T is O or S; and
X is hydrogen or a leaving group selected from the group consisting of mesylates, sulfonates and halogen (Cl, Br and I);
and their isolated enantiomers, diastereoisomers or mixtures thereof.

14. The method of claim 13, wherein the method provides a higher concentration of the cancer chemotherapeutic agent in a cancer cell of the patient.

15. The method of claim 14, wherein the method delivers a higher concentration of the cancer chemotherapeutic agent in the cancer cell, when compared to the administration of a non-conjugated cancer chemotherapeutic agent to the patient, by at least 5%, 10%, 20% or at least 50%.

* * * * *